United States Patent
Baura et al.

(10) Patent No.: US 7,570,989 B2
(45) Date of Patent: Aug. 4, 2009

(54) METHOD AND APPARATUS FOR SIGNAL ASSESSMENT INCLUDING EVENT REJECTION

(75) Inventors: Gail D. Baura, San Diego, CA (US); Jeremy Malecha, San Diego, CA (US); Radouane Bouguerra, Poway, CA (US)

(73) Assignee: Cardiodynamics International Corporation, San Diego, CA (US)

( * ) Notice: Subject to any disclaimer, the term of this patent is extended or adjusted under 35 U.S.C. 154(b) by 407 days.

(21) Appl. No.: 10/995,920

(22) Filed: Nov. 22, 2004

(65) Prior Publication Data
US 2006/0111642 A1    May 25, 2006

(51) Int. Cl.
*A61B 5/0402* (2006.01)
(52) U.S. Cl. .................................. 600/513
(58) Field of Classification Search ............ 600/300, 600/301, 481–523
See application file for complete search history.

(56) References Cited

U.S. PATENT DOCUMENTS

| | | | |
|---|---|---|---|
| RE30,101 E | 9/1979 | Kubicek et al. | |
| 4,802,491 A | 2/1989 | Cohen et al. | |
| 5,010,888 A | 4/1991 | Jadvar et al. | |
| 5,101,828 A | 4/1992 | Welkowitz et al. | |
| 5,178,151 A | 1/1993 | Sackner | |
| 5,178,154 A | 1/1993 | Ackmann et al. | |
| 5,184,620 A | 2/1993 | Cudahy et al. | |
| 5,277,189 A | 1/1994 | Jacobs | |
| 5,287,520 A | 2/1994 | Kaiser | |
| 5,309,917 A * | 5/1994 | Wang et al. | 600/508 |
| 5,311,874 A | 5/1994 | Baumann et al. | |
| 5,390,679 A | 2/1995 | Martin | |
| 5,391,199 A | 2/1995 | Ben-Haim | |
| 5,423,326 A | 6/1995 | Wang et al. | |
| 5,439,483 A | 8/1995 | Duong-Van | |
| 5,442,543 A | 8/1995 | Tresp | |
| 5,443,073 A | 8/1995 | Wang et al. | |

(Continued)

FOREIGN PATENT DOCUMENTS

WO    WO 2002/079776    10/2002

OTHER PUBLICATIONS

Non-Invasive Hemodynamic Monitoring with BioZ.RTM.Impedance Cardiography web page (2 pages).

(Continued)

*Primary Examiner*—Scott M Getzow
(74) *Attorney, Agent, or Firm*—Gazdzinski & Associates, PC

(57) ABSTRACT

An improved method and apparatus for non-invasively assessing one or more physiologic parameters, such as for example those associated with the circulatory system of a living organism. In one exemplary embodiment, the invention evaluates cardiac events (e.g., beats) present within an ECG waveform to determine which beats should be retained and which rejected. This evaluation is conducted based on a hierarchical method, wherein the ECG noise and morphology, as well as various aspects of the Delta Z (change in thoracic impedance), are utilized to evaluate beats for retention/rejection. In one variant, fuzzy models are used in conducting the foregoing evaluations. Parameter median filtering is also optionally applied. The foregoing techniques increase the accuracy, stability and robustness of any systems (e.g., impedance cardiographic or otherwise) which make use of the events. Improved impedance cardiographic apparatus and methods of treatment are also disclosed.

45 Claims, 20 Drawing Sheets

U.S. PATENT DOCUMENTS

| | | | |
|---|---|---|---|
| 5,505,209 | A | 4/1996 | Reining |
| 5,511,553 | A | 4/1996 | Segalowitz |
| 5,543,795 | A | 8/1996 | Fernald |
| 5,546,951 | A | 8/1996 | Ben-Haim |
| 5,590,648 | A | 1/1997 | Mitchell et al. |
| 5,634,465 | A | 6/1997 | Schmiesing et al. |
| 5,685,316 | A | 11/1997 | Schookin et al. |
| 5,730,142 | A | 3/1998 | Sun et al. |
| 5,778,881 | A | 7/1998 | Sun et al. |
| 5,782,888 | A | 7/1998 | Sun et al. |
| 5,876,351 | A | 3/1999 | Rohde |
| 5,895,298 | A | 4/1999 | Faupel et al. |
| 5,902,325 | A | 5/1999 | Condie et al. |
| 5,913,826 | A | 6/1999 | Blank |
| 5,967,995 | A | 10/1999 | Shusterman et al. |
| 5,999,845 | A | 12/1999 | dePinto |
| 6,007,491 | A | 12/1999 | Ling et al. |
| 6,016,445 | A | 1/2000 | Baura |
| 6,022,322 | A | 2/2000 | Prutchi |
| 6,099,477 | A | 8/2000 | Archibald et al. |
| 6,115,628 | A | 9/2000 | Stadler et al. |
| 6,128,526 | A | 10/2000 | Stadler et al. |
| 6,141,575 | A | 10/2000 | Price |
| 6,161,038 | A * | 12/2000 | Schookin et al. ............ 600/519 |
| 6,186,955 | B1 | 2/2001 | Baura |
| 6,249,595 | B1 | 6/2001 | Foxall et al. |
| 6,253,103 | B1 | 6/2001 | Baura |
| 6,281,681 | B1 | 8/2001 | Cline et al. |
| 6,292,689 | B1 | 9/2001 | Wallace et al. |
| 6,310,967 | B1 | 10/2001 | Heine et al. |
| 6,326,971 | B1 | 12/2001 | Van Wieringen |
| 6,370,424 | B1 | 4/2002 | Prutchi |
| D468,433 | S | 1/2003 | Wagner et al. |
| D471,281 | S | 3/2003 | Baura et al. |
| D475,138 | S | 5/2003 | Baura et al. |
| 6,561,986 | B2 | 5/2003 | Baura et al. |
| 6,602,201 | B1 | 8/2003 | Hepp et al. |
| 6,636,754 | B1 | 10/2003 | Baura et al. |
| 7,043,293 | B1 | 5/2006 | Baura |
| 7,149,576 | B1 | 12/2006 | Baura et al. |
| 7,214,107 | B2 | 5/2007 | Powell et al. |
| 7,251,524 | B1 | 7/2007 | Hepp et al. |
| 2003/0013978 | A1 * | 1/2003 | Schlegel et al. ............ 600/509 |
| 2007/0058488 | A1 * | 3/2007 | Lerro et al. ............ 367/99 |

OTHER PUBLICATIONS

Sorba Medical Systems—product literature regarding the Steorra TM. impedance cardiograph—consisting of three (3) pages.

Solar.RTM.800M Patient Monitor GE Medical Systems web page (6 pages).

B. Bo Sramck, MSEE, "Hemodynamic and Pump-Performance Monitoring by Electrical Bioimpedance," Problems in Respiratory Care. vol. 2, No. 2, pp. 274-290, Apr./Jun. 1989.

G. D. Baura, Ph.D., et al., "Intra-Sensor Spacing and Sensor Placement Variablity on Impedance Cardiography (ICG) Parameters," CDIC Technical Report #TR-048, consisting of 2 pages, Jul. 20, 2000.

GE Medical Systems Information Technologies, "Non-Invasive Hemodynamic Monitoring With BioZ Impedance Cardiography," consisting of 2 pages, 2001.

Wantagh, Incorporated, "Noninvasive Continuous Hemodynamic Monitoring," pp. 1-4 (date unknown).

Sorba Medical Systems—product literature regarding the CIC-1000. TM.-consisting of two (2) pages.

Sorba Medical Systems—product literature entitled "Transthoracic Electrical Bioimpedance R-wave Triggered Ensemble" Averaging consisting of four (4) pages.

Lead-Lok, Inc., (Aug. 8, 1998), Final Production Specifications consisting of two (2) pages.

Nyboer, Jan, Sc.D. , M.D., et al., (1950), "Electrical Impedance Plethysmography," Circulation, vol. II, pp. 811-821.

Kubicek, W.G., et al., (1966). "Development and Evaluation of An Impedance Cardiac Output System," Aerospace Med., 37:1208-1212.

Lababidi, Z. et al., (1970) "The First Derivative Thoracic Impedance Cardiogram," Circulation, 41:651-658.

Sramck, B.B., (1982). "Cardiac Output by Electrical Impedance," Med. Elect, 13:93-97.

Bernstein, D.P., (1986), "A New Stroke Volume Equation for Thoracic Electrical Bioimpedance: Theory and Rationale," Critical Care Med., 14:904-909.

Li. C., et al., (1995), "Detection of ECG Characteristic Points Using Wavelet Transforms," IEEE Trans. BME. vol. 42, No. 1, pp. 21-28.

Kadambe, S., et al., (1995), "Wavelet Transform-Based QRS Complex Detector." IEEE Trans, BME, vol. 46, No. 7, pp. 838-848.

Afonso, V. X., et al., (1999). "ECG Beat Detection Using Filter Banks," IEEE Trans. BME, vol. 46, No. 2, pp. 838-848.

Newman, D.G., et al., (1999), "The Non-Invasive Assessment of Stroke Volume and Cardiac Output by Impedance Cardiography: A Review," Aviation, Space, and Environmental Medicine, vol. 70, No. 8, pp. 780-789.

* cited by examiner (Part 1 of 2)

(Part 2 of 2)

(Part 1 of 3)

(Part 2 of 3)

(Part 3 of 3)

METHOD AND APPARATUS FOR SIGNAL ASSESSMENT INCLUDING EVENT REJECTION

RELATED APPLICATIONS

This application is related to co-owned and co-pending U.S. patent application Ser. No. 10/329,129 filed Dec. 24, 2002 and entitled "Method and Apparatus for Waveform Assessment", incorporated herein by reference in its entirety.

COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to the field of signals analysis, and in one exemplary aspect to an apparatus and method for non-invasively detecting and evaluating signals and waveforms such as those present in the impedance cardiograms, electrocardiograms, and other physiologic parameters of a living subject.

2. Description of Related Technology

The study of the performance and properties of the physiology (including notably the cardiovascular system) of a living subject has proven useful for diagnosing and assessing any number of conditions or diseases within the subject. The performance of the cardiovascular system, including the heart, has characteristically been measured in terms of several different parameters, including the stroke volume and cardiac output of the heart.

Noninvasive estimates of cardiac output (CO) can be obtained using the well known technique of impedance cardiography (ICG). Strictly speaking, impedance cardiography, also known as thoracic bioimpedance or impedance plethysmography, is used to measure the stroke volume (SV) of the heart. As shown in Eqn. (1), when the stroke volume is multiplied by heart rate, cardiac output is obtained.

$$CO = SV \times \text{heart rate}. \quad (1)$$

During impedance cardiography, a constant alternating current, with a frequency such as 70 kHz, $I(t)$, is applied across the thorax. The resulting voltage, $V(t)$, is used to calculate impedance. Because the impedance is assumed to be purely resistive, the total impedance, $Z_T(t)$, is calculated by Ohm's Law. The total impedance consists generally of a constant base impedance, $Z_o$, and time-varying impedance, $Z_c(t)$, as shown in Eqn. (2):

$$Z_T(t) = \frac{V(t)}{I(t)} = Z_o + Z_c(t). \quad (2)$$

The time-varying impedance is believed to reflect the change in blood resistivity as it transverses through the aorta.

Stroke volume is typically calculated from one of three well known equations, based on this impedance change:

$$\text{Kubicek:} \quad SV = \rho \left(\frac{L^2}{Z_0^2}\right) LVET \frac{dZ(t)}{dt_{\max}}, \quad (3)$$

$$\text{Sramek:} \quad SV = \frac{L^3}{4.25 Z_o} LVET \frac{dZ(t)}{dt_{\max}}, \quad (4)$$

$$\text{Sramek-Berstein:} \quad SV = \delta \frac{(0.17H)^3}{4.25 Z_o} LVET \frac{dZ(t)}{dt_{\max}}. \quad (5)$$

Where:
L=distance between the inner electrodes in cm,
LVET=ventricular ejection time in seconds,
$Z_o$=base impedance in ohms, $\frac{dZ(t)}{dt_{\max}}$ = magnitude of the largest negative derivative of the impedance change, $Z_c(t)$, occurring during systole in ohms/s,
$\rho$=resistivity of blood in ohms-cm,
H=subject height in cm, and
$\delta$=special weight correction factor.

Two key parameters present in Eqns. 3, 4, and 5 above are (i)

$$\frac{dZ(t)}{dt_{\max}}$$

and (ii) LVET.

These parameters are found from features referred to as fiducial points, that are present in the inverted first derivative of the impedance waveform, $$\frac{dZ(t)}{dt}.$$

As described by Lababidi, Z., et al, "The first derivative thoracic impedance cardiogram," Circulation, 41:651-658, 1970, the value of $$\frac{dZ(t)}{dt_{\max}}$$

is generally determined from the time at which the inverted derivative value has the highest amplitude, also commonly referred to as the "C point". The value of $$\frac{dZ(k)}{dt_{\max}}$$

is calculated as this amplitude value. LVET corresponds generally to the time during which the aortic valve is open. That point in time associated with aortic valve opening, also commonly known as the "B point", is generally determined as the time associated with the onset of the rapid upstroke (a slight inflection) in $$\frac{dZ(t)}{dt}$$

before the occurrence of the C point. The time associated with aortic valve closing, also known as the "X point", is generally determined as the time associated with the inverted derivative global minimum, which occurs after the C point.

In addition to the foregoing "B", "C", and "X" points, the so-called "O point" may be of utility in the analysis of the cardiac muscle. The O point represents the time of opening of the mitral valve of the heart. The O point is generally determined as the time associated with the first peak after the X point. The time difference between aortic valve closing and mitral valve opening is known as the isovolumetric relaxation time, IVRT. However, to date, the O point has not found substantial utility in the stroke volume calculation.

Impedance cardiography further requires recording of the subject's electrocardiogram (ECG) in conjunction with the thoracic impedance waveform previously described. Processing of the impedance waveform for hemodynamic analysis generally requires the use of ECG fiducial points as landmarks. Processing of the impedance waveform is generally performed on a beat-by-beat basis, with the ECG being used for beat detection. In addition, detection of some fiducial points of the impedance signal may require the use of ECG fiducial points as landmarks. Specifically, individual beats are identified by detecting the presence of QRS complexes within the ECG. The peak of the R wave (commonly referred to as the "R point") in the QRS complex is also detected, as well as the onset of depolarization of the QRS complex ("Q point").

Under the prior art approaches, the aforementioned beats are scrutinized for artifact (e.g., due to motion of the subject, or other such causes), through comparatively simple rules such as the evaluation of calculated parameter values outside a typical numeric range. For example, consider the well-known "Weissler window", which defines the X point search interval based upon the heart rate and gender of a given individual; see, Weissler, A. M., Peeler, R. G., Roehll, W. H., "Relationships between left ventricular ejection time, stroke volume, and heart rate in normal individuals and patients with cardiovascular disease", Am Heart J, 62:367-78, 1961. The Weissler regression equation was based upon 121 normal males, and 90 normal females. Although the relationship between heart rate and LVET is linear for normal individuals, in another work Weissler et. al. found that this relationship does not hold for abnormal patients. In 12 non-valvular CHF patients with COs ranging from 2.1-5.8 L/min, 9 patients had a significant decrease (p<0.05) in ejection time relative to heart rate; see Weissler, A. M., Harris, W S., and Schoenfeld, C. D., "Systolic Time Intervals in Heart Failure in Man. Circulation", 37:149-59, 1968. Hence, when applying such criteria, the true X points in CHF or other cardiovascular patients may be erroneously rejected because these X points lie outside of the Weissler window.

Other such "parametric" rejection rules may include for example (i) LVET outside of a desired range, (ii) detection of a pacing spike with the left/right values of ΔZ(t) (also referred to as Delta Z), (iii) $d^2Z/dt^2{}_{MAX}=0$, and (iv) $dZ/dt_{MAX}=0$ (or less than a percentage of the median value of the most recent beats).

Parameter values from the remaining beats (i.e., those not rejected by the aforementioned parametric criteria) are then typically averaged as a mean, based on a beat average number chosen by the user.

Aside from erroneous rejection of beats as described above in the context of the Weissler window, other problems with prior art beat analysis and rejection approaches exist. Specifically, significant instabilities in various of the monitored or derived parameters such as ECG, and left/right ΔZ(t) can result. Such instabilities can reduce both the accuracy and clinical robustness of the measurement process. Erroneous pacing spike detection may also occur during a time interval that does not overlap with a valid B, C, or X point. Additionally, when the electrodes are disconnected, the "flat-line" ECG and Delta Z signals may provide a non-zero cardiac output (CO) estimate.

Still another distinct deficiency with the prior art analysis and rejection schemes relates to their lack of discrimination between different types of subjects. This lack of discrimination has two primary outgrowths: (i) causing the system to simply not function due to being unable to measure one or more necessary parameters; and (ii) imbuing the user or operator with somewhat of a false sense of security that all types of subjects (regardless of their peculiar waveforms, arrhythmias or defects) could be successfully monitored, including generating highly suspect or even erroneous data without otherwise alerting the user as to the potential for degraded accuracy. Without any sort of contraindication (or even metric advising on the confidence level of the data or results), the user/operator has no way of knowing, other than perhaps via innate experience or knowledge, whether any given data is valid or accurate.

Fuzzy Logic and Fuzzy Models

As is well known in the art, so-called "fuzzy logic" is a superset of conventional (Boolean) logic that has been extended to handle the concept of partial truth; i.e., truth values falling between "completely true" and "completely false". Fuzzy logic was invented by Dr. Lotfi Zadeh of U.C. Berkeley in 1965. The fuzzy model, which utilizes fuzzy logic, is a problem-solving control system methodology that lends itself to implementation in systems ranging from simple, small, embedded micro-controllers to large, networked, multi-channel PC or workstation-based data systems. It can be implemented in hardware, software, or a combination of both. The fuzzy model provides a comparatively simple technique for arriving at a definite conclusion based upon vague, ambiguous, imprecise, noisy, or missing input information, and in some aspects mimics the human decision making process.

As is well understood in the prior art, a fuzzy model incorporates alternative, rule-based mathematics (e.g., If X AND Y THEN Z), as opposed to attempting to model a system or its response using closed-form mathematical equations. When the number of model inputs and model outputs are limited to two each, the fuzzy model is in general empirically-based, relying on an empirical data (such as prior observations of parameters or even an operator's experience).

Specifically, a subset U of a set S can be defined as a set of ordered pairs, each with a first element that is an element of the set S, and a second element that is an element of the set {0, 1}, with exactly one ordered pair present for each element of S. This relationship defines a mapping between elements of S and elements of the set {0, 1}. Here, the value "0" is used to represent non-membership, and the value "1" is used to rep resent membership. The truth or falsity of the exemplary statement:

A is in U is determined by finding the ordered pair whose first element is A. The foregoing statement is true if the second element of the ordered pair is "1", and the statement is false if it is "0". Similarly, a fuzzy subset F of set S can be defined as a set of ordered pairs, each having a first element that is an element of the set S, and a second element that is a value falling in the interval [0, 1], with exactly one ordered pair present for each element of S. This defines a mapping between elements of the set S and values in the interval [0, 1]. The value zero is used to represent complete non-membership, the value one is used to represent complete membership, and values in between are used to represent intermediate degrees of membership. These fuzzy subsets serve as the fuzzy inputs and outputs of a fuzzy model, whose input-output relationship is defined by a rule base table.

Inherent benefits of the fuzzy model relate to its speed and simplicity of processing (e.g., MIPS, FLOPS, or similar benchmark), and its ability to process data that is not easily represented in closed-form equations, such as may occur in physiologic data. The benefits are particularly useful the analysis of time-variant "noisy" signals where detection, identification, and/or evaluation of one or more features or events of the waveform are required, such as electrocardiography, impedance cardiography, or electroencephalography.

Based on the foregoing, what is needed are improved methods and apparatus for assessing physiologic (e.g., hemodynamic) parameters, including cardiac output, within a living subject. Such method and apparatus would ideally be completely non-invasive, accurate, easily adapted to the varying physiology of different subjects, and would produce reliable and stable results under a variety of different operating conditions. These methods and apparatus would be particularly adapted to processing (and rejecting, where warranted) "noisy" waveforms having events such as cardiac beats, and would allow for monitoring of a broader range of patient types and conditions (including various arrhythmias).

SUMMARY OF THE INVENTION

The present invention satisfies the aforementioned needs by an improved method and apparatus for, inter alia, non-invasively assessing physiologic parameters (including cardiac output) within a living subject.

In a first aspect of the invention, an improved method of assessing cardiac output within a living subject is disclosed. In one embodiment, the method comprises: disposing a plurality of electrodes relative to the thoracic cavity of the subject; passing an electrical current through at least a portion of the thoracic cavity; measuring at least one impedance waveform associated with the thoracic cavity using the current and at least one of the plurality of electrodes; measuring at least one electrocardiographic waveform having a plurality of events associated therewith; selectively rejecting at least one of the events; and determining cardiac output based at least in part on the impedance waveform and at least a portion of the non-rejected ones of the events. The events comprise, e.g., cardiac beats within the electrocardiographic waveform, and the act of selectively rejecting comprises performing analysis based on various aspects of the ECG signal (e.g., noise and/or morphology) as well as the impedance waveform (e.g., similarity and/or reproducibility).

In a second aspect of the invention, an improved method of assessing a hemodynamic parameter within a living subject is disclosed. In one embodiment, the method comprises: disposing at least one electrode relative to the subject; measuring at least one cardiographic waveform from the subject using the at least one electrode, the waveform having a plurality of beats; processing the plurality of beats to identify first beats that should be rejected, and second beats that should not be rejected; and assessing the hemodynamic parameter based at least in part on the second beats.

In a third aspect of the invention, an improved apparatus adapted to evaluate the cardiac beats of a living subject is disclosed. In one embodiment, the apparatus uses at least one fuzzy-based noise algorithm and at least one fuzzy-based morphology algorithm to screen beats for possible rejection. A rule base inference (RBI) process based on a Zadeh intersection approach is used in combination with a centroid-based defuzzification process.

In a fourth aspect of the invention, an improved impedance cardiographic apparatus adapted to evaluate physiologic waveforms obtained from a living subject is disclosed. In one embodiment, the apparatus uses a computer program adapted to evaluate criteria comprising (i) at least one ECG rejection criterion and (ii) at least one Delta Z rejection criterion.

In a fifth aspect of the invention, improved cardiographic apparatus adapted to evaluate the cardiac beats of a living subject is disclosed. In one embodiment, the apparatus performs an ECG rejection analysis; a Delta Z rejection analysis; and a median filtering analysis. The ECG, Delta Z and median filtering processes are performed in a substantially sequential hierarchy.

In a sixth aspect of the invention, an improved method of evaluating the cardiac beats of a living subject is disclosed. In one embodiment, the method comprises: performing an ECG rejection analysis; performing a Delta Z rejection analysis; and performing a median filtering analysis.

In a seventh aspect of the invention, an improved method of evaluating the cardiac beats of a living subject is disclosed. In one embodiment, the method comprises: performing a beat rejection analysis on a plurality of the cardiac beats; rejecting at least one of the beats as part of the analysis; and determining, based at least in part on the at least one rejected beat, a status of the rejection analysis. The status of the analysis may comprise the suitability of the (ECG) inputs to the analysis, or the suitability of the analysis itself at accurately rejecting (or retaining) beats.

In another embodiment, the method comprises: providing a plurality of sources of the cardiac beats; performing a beat rejection analysis on a plurality of the cardiac beats derived from a first of the plurality of sources; rejecting at least one of the beats as part of the analysis; and determining, based at least in part on the at least one rejected beat, the suitability of the first source for providing the cardiac beats. If the first source is determined to be (or possibly) unsuitable, a secondary process such as an automatic ECG vector selection routine, is employed to select one or more optimal sources.

In an eighth aspect of the invention, improved cardiographic apparatus is disclosed. In one embodiment, the apparatus comprises an ECG evaluation module and a plurality of input vectors associated therewith, the module evaluating the cardiac beats of a living subject represented by one or more of the vectors. The module evaluates the beats by: providing a plurality of sources of the cardiac beats; performing a beat rejection analysis on a plurality of the cardiac beats derived from a first of the plurality of sources; rejecting at least one of the beats as part of the analysis; and determining, based at least in part on the at least one rejected beat, the suitability of the first source for providing the cardiac beats.

DETAILED DESCRIPTION OF THE INVENTION

Figure 1:
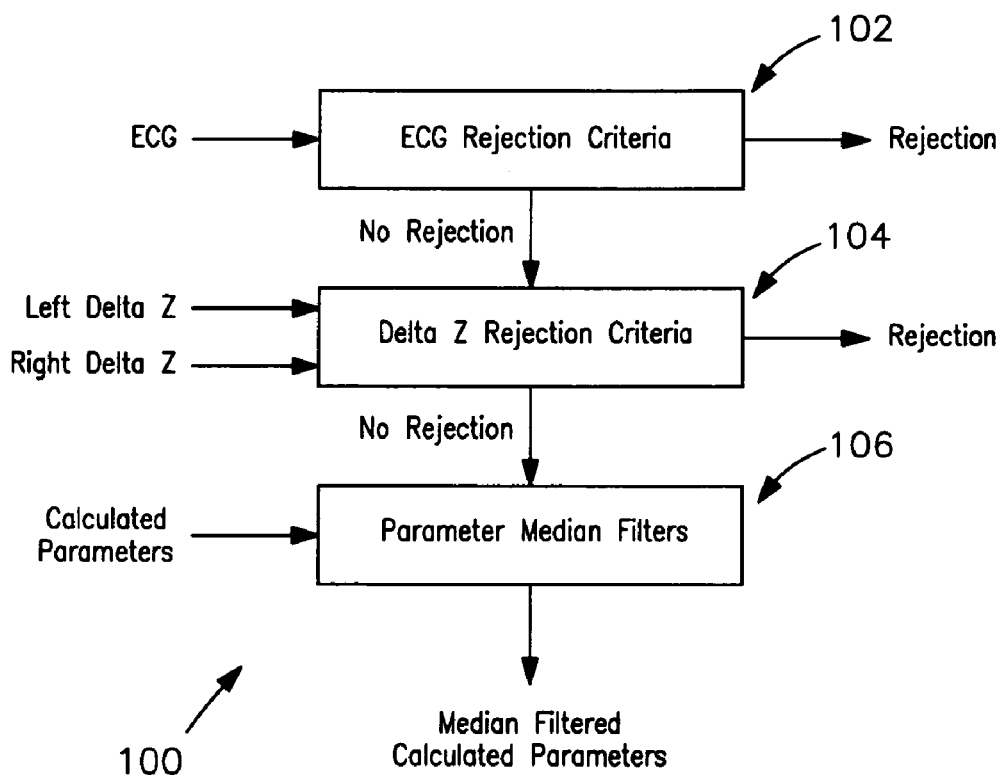
FIG. 1 is a graphical representation of one exemplary embodiment of the analytical hierarchy used for processing waveform events according to the present invention.

Reference is now made to the drawings wherein like numerals refer to like parts throughout.

It is noted that while the invention is described herein in terms of an apparatus and method for analyzing waveforms and signals derived from the thorax of a human subject, the invention may also be embodied or adapted to monitor other locations on the human body, as well as monitoring parameters of other warm-blooded species such as, for example, primates, canines, or porcines. All such adaptations and alternate embodiments are considered to fall within the scope of the claims appended hereto.

As used herein, the term "signal" refers to any electrical, optical, electromagnetic, subatomic, thermal, chemical/electro-chemical, or other transferal of information. Such signal may be, without limitation, in the analog or digital domain, or otherwise. Specific examples of signals include waveforms, pulses, binary digital data, analog voltage levels, modulated radio or infrared waves, including temporal and/or spatial variations of any of the foregoing.

As used herein, the term "morphology" refers generally to the property of shape and/or appearance of an event or artifact, including without limitation that associated with cardiac waveforms. The term "morphology" may refer to non-physiologic waveforms as well.

As used herein, the term "module" refers generally to a logical sequence or association of steps, processes or components. For example, a software module might comprise a set of associated routines or subroutines within a computer program. Alternatively, a module might comprise a substantially self-contained hardware device. A module might also comprise a logical set of processes irrespective of any software or hardware implementation.

As used herein, the term "network" refers generally to any type of telecommunications or data network including, without limitation, hybrid fiber coax (HFC) networks, satellite networks, telco networks, and data networks (including MANs, WANs, LANs, WLANs, internets, and intranets). Such networks or portions thereof may utilize any one or more different topologies (e.g., ring, bus, star, loop, etc.), transmission media (e.g., wired/RF cable, RF wireless, infrared, millimeter wave, optical, etc.) and/or communications or networking protocols (e.g., SONET, DOCSIS, IEEE Std. 802.3, 802.11, 802.15, Bluetooth, ATM, X.25, Frame Relay, 3GPP, 3GPP2, WAP, SIP, UDP, FTP, RTP/RTCP, H.323, etc.).

As used herein, the terms "client device" and "end user device" include, but are not limited to, personal computers (PCs) and minicomputers, whether desktop, laptop, or otherwise, personal digital assistants (PDAs) such as the Apple Newton®, "Palm®" family of devices, handheld computers, personal communicators such as the Motorola Accompli or V710, J2ME equipped devices, cellular telephones, wireless nodes, or literally any other device capable of interchanging data with a network.

As used herein, the term "application" refers generally to a unit of executable software that implements a certain functionality or theme. The themes of applications vary broadly across any number of disciplines and functions, and one application may have more than one theme. The unit of executable software generally runs in a predetermined environment; for example, the unit could comprise a module that runs within the Java™ environment.

As used herein, the term "computer program" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as the Common Object Request Broker Architecture (CORBA), Java™ (including J2ME, Java Beans, etc.) and the like.

As used herein, the term "server" refers to any computerized component, system or entity regardless of form which is adapted to provide data, files, applications, content, or other services to one or more other devices or entities on a computer network.

Overview

In one fundamental aspect, the present invention comprises a method of assessing physiologic (e.g., hemodynamic) parameters within a living subject through analysis of continuous or non-continuous waveforms, including artifacts within these waveforms. This assessment includes enhanced or "intelligent" rejection of certain portions of the waveform(s). By accurately rejecting or not rejecting these portions of the analyzed signals, greater accuracy and clinical robustness are provided. Furthermore, a greater level of confidence in the physiologic data obtained (or data derived therefrom) is also provided through use of this approach.

In one exemplary embodiment, the foregoing methods and apparatus are adapted to the measurement of impedance cardiograms (ICG) and/or electrocardiograms (ECG) for living subjects. Specifically, more robust rejection of waveform events of interest (such as cardiac beats) is provided through use of a hierarchy or class system, as well as the application of advanced fuzzy logic models, cross-correlation techniques, and beat averaging.

In a first exemplary rejection class, a cardiac beat is excluded if it does not meet the ECG criteria for minimum ECG amplitude, heart rate range, noise, and/or morphology (i.e., shape and/or appearance). The ECG noise and morphology rejection criteria are based on fuzzy models, although other approaches may be employed.

In a second exemplary rejection class, a beat is excluded if it does not meet the prescribed criteria for minimum Delta Z amplitude, similarity, and/or reproducibility. The Delta Z noise rejection criteria are also optionally based on fuzzy models.

In a third exemplary rejection class, all calculated parameters are optionally median filtered so that extremely high or low parameter values are never displayed or utilized.

FIG. 1 (discussed in greater detail below) graphically illustrates one embodiment of this exemplary assessment and rejection hierarchy at a high level.

The foregoing artifact analysis and rejection hierarchy advantageously provides a number of other benefits, including enabling the accurate monitoring of the majority of patients with arrhythmias/conduction defects, and highly stable ECG and Delta Z parameter updates. More stable parameter displays are also provided, which give the user or operator a tangible perception of the improved accuracy referenced above.

Furthermore, while the methods and apparatus of the present invention find great utility in the field of hemodynamic measurement and assessment, these methods and apparatus (when properly adapted) may be more broadly applied to other non-hemodynamic parameters, and even non-physiologic systems wherein the evaluation of a periodic series of waveform events requires analysis such as, without limitation, pulsed radio frequency (RF) systems and pulsed Doppler-based acoustic underwater systems such as active sonar and ADCPs.

Description of Exemplary Embodiments

Figure 1A:
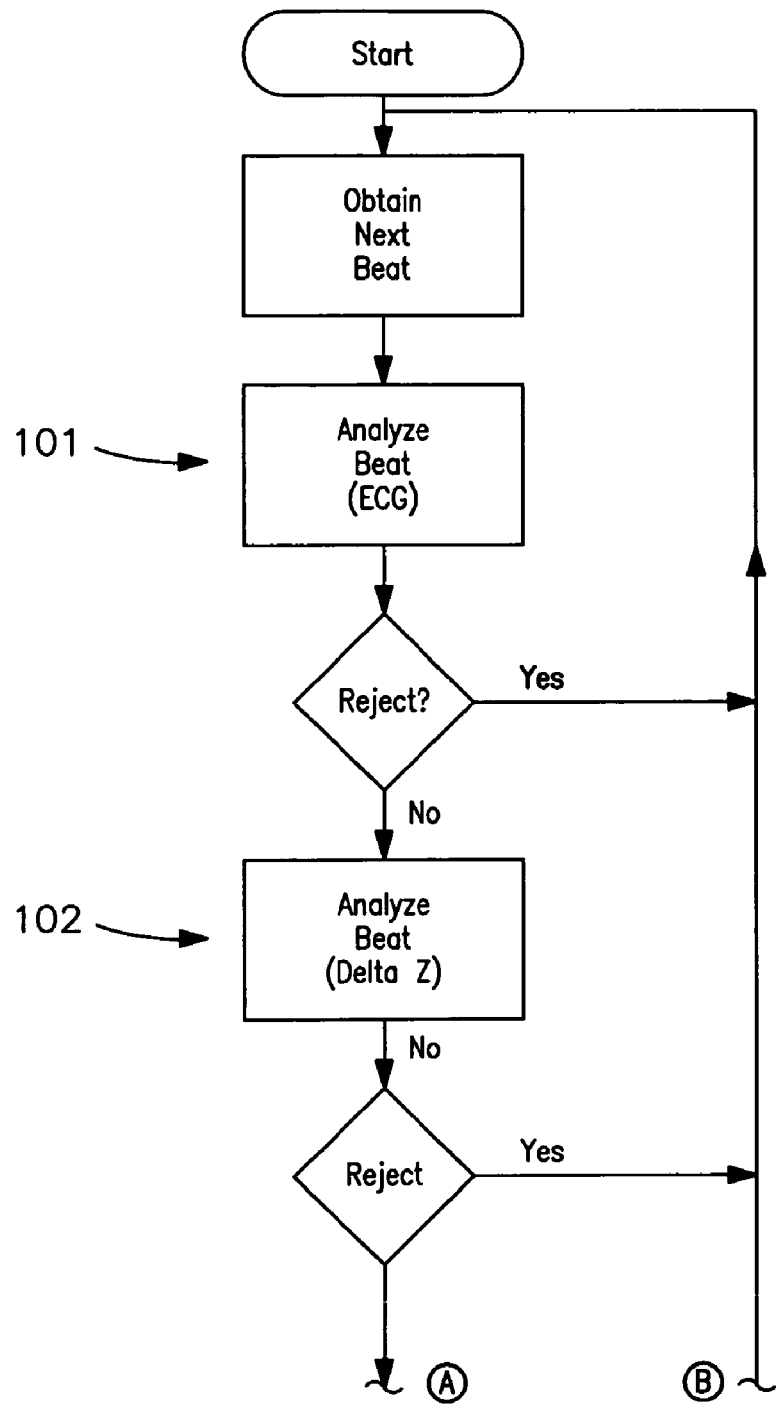
FIG. 1a is a logical block diagram illustrating one exemplary embodiment of the waveform analysis methodology of the present invention.
Figure 1A:
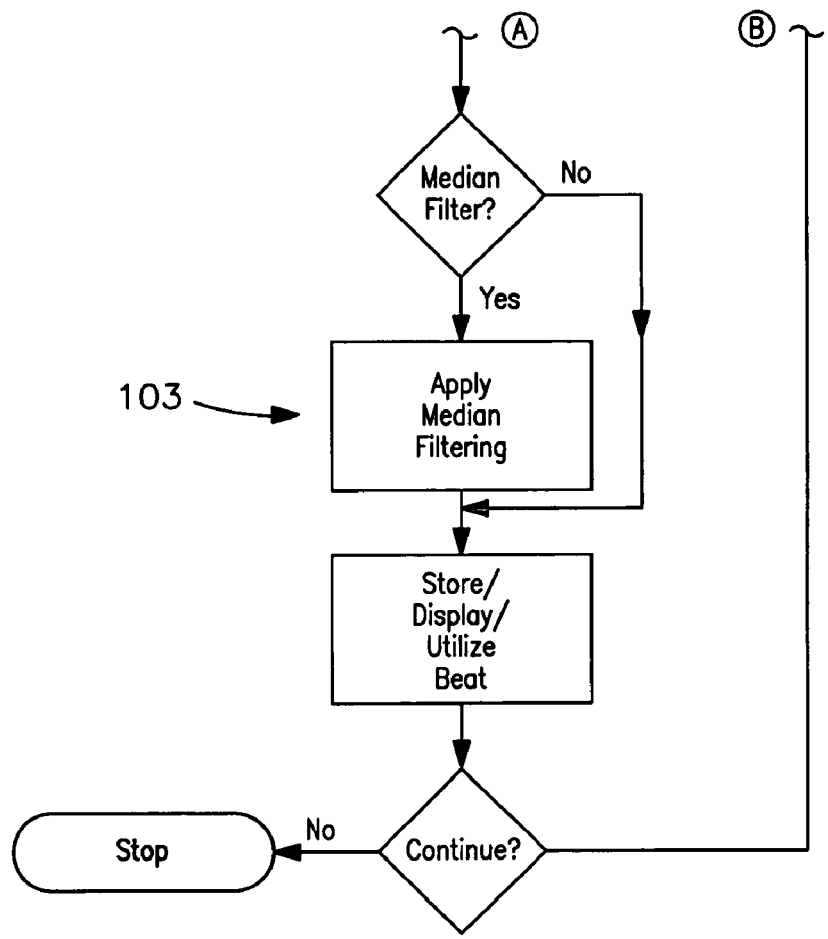

Referring now to FIGS. 1 and 1a, a first exemplary embodiment of the artifact analysis methodology of the present invention is described It will be appreciated that while described primarily in the context of cardiac events (i.e., beats), the methods and apparatus of the invention may be applied to events occurring in other (non-cardiac) waveforms As shown in FIG. 1, the exemplary analysis model includes an analytical hierarchy 100 comprising three classes 102, 104, 106 of rejection.

In the first rejection class 102, an artifact (e.g., beat) is excluded if it does not meet the ECG criteria which may include ECG amplitude, heart rate, noise, and/or morphology.

In the second rejection class, a beat is excluded if it does not meet the criteria for Delta Z amplitude, similarity and/or reproducibility.

In the third rejection class, all calculated parameters are median filtered so that extremely high or low parameter values are never displayed. These criteria are discussed in detail in the following sections.

An assumption for the rejection hierarchy of FIG. 1 is that so-called "R" points are detected accurately. It will be appreciated, however, that the methodology of the present invention has some degree of robustness in this regard, such that useful results can be derived even when the R point detection is less than optimal.

ECG Rejection Criteria—

Figure 2:
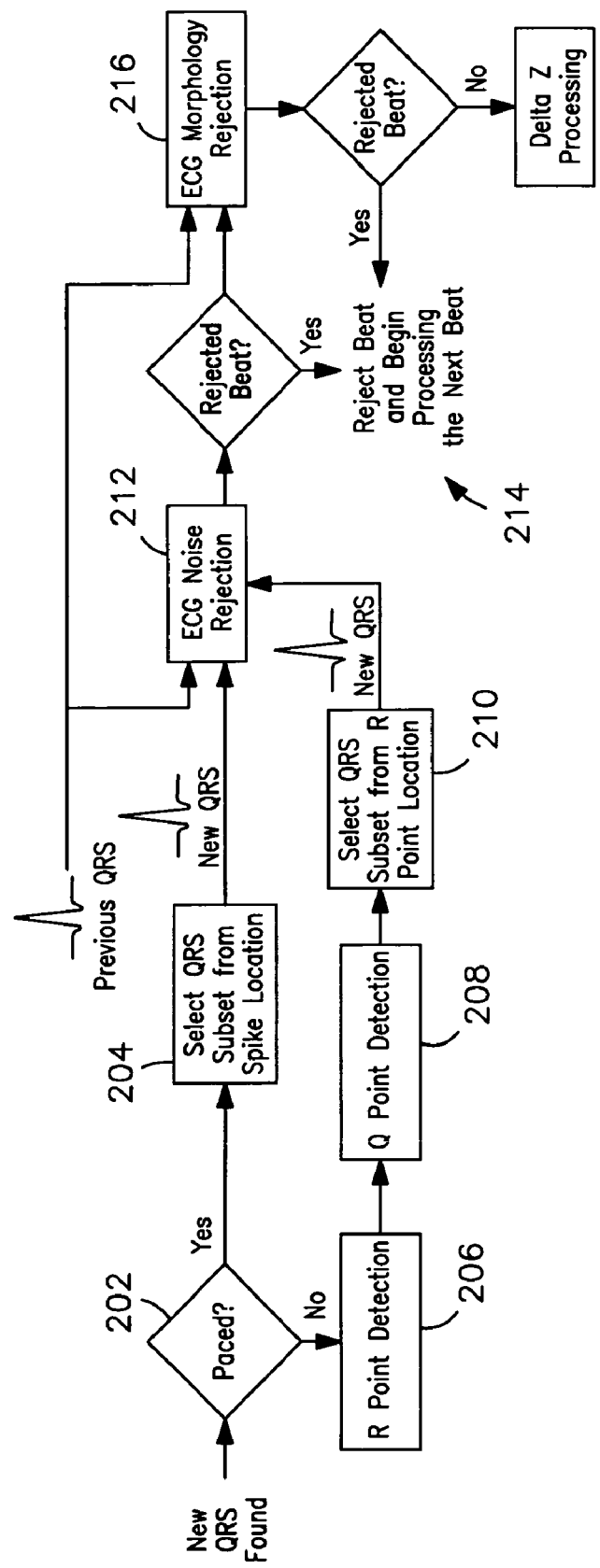
FIG. 2 is a graphical representation of one exemplary embodiment of the ECG module event rejection processing according to the invention, including ECG noise and morphology analyses.

Referring now to FIG. 2, a first exemplary embodiment of the ECG rejection criteria methodology (step 102 of FIG. 1) is described. In this embodiment, the ECG rejection criteria are advantageously based on Association for the Advancement of Medical Instrumentation (AAMI) and/or other relevant standards and specifications in order to provide maximum applicability and uniformity, although it will be recognized this is not a requirement of the invention.

As will be recognized by those of ordinary skill, the ECG is generally less sensitive than Delta Z to noise artifact, and hence is used in the exemplary embodiment to parse Delta Z beats. However, when high levels of noise are present, detection of pacemaker spikes and R points may be unreliable, and hence may be avoided.

Furthermore, as described subsequently herein, "flat-line" signals (i.e., signals with no time/amplitude variance), and signals relating to very low or high patient heart rates, are rejected.

According to one salient aspect of the invention, "noisy" and/or dissimilar beats are rejected using at least one of the ECG noise and morphology rejection methodologies which, in an exemplary apparatus configuration, comprise computer program routines running on a digital processor (see discussion of FIG. 14 below). The interaction of these two algorithms is illustrated in FIG. 2.

As shown in FIG. 2, the new QRS complex is first analyzed to determine whether pacing is applicable (step 202). If so, a QRS subset is selected from the pacing spike location (step 204). If not, the R point is detected (step 206), the Q point detected (step 208), and the QRS subset selected from the R point location (step 210).

The new QRS (whether from the pacing or non-pacing branches described above) are then analyzed relative to the previous QRS complex based on the ECG noise rejection criteria (described subsequently herein) per step 212. If the beat is rejected, the next beat is analyzed (step 214). If no rejection occurs, the ECG morphology analysis is next performed (step 216). If the beat survives the morphology testing, it is then passed to Delta Z processing per step 220. Otherwise, the next beat is analyzed per step 214.

In one embodiment of the method 200 of FIG. 2, R point detection occurs when a paced QRS occurs (i.e., after the pacing spike detection, but before noise rejection). This means that the QRS subsets for both paced and unpaced beats are centered around the same feature, the R point. However, it will be recognized that other approaches may be utilized.

The illustrated embodiment of the ECG noise and morphology rejection algorithms (FIG. 2) assumes that a 'good' or normal beat is stored as a prior QRS complex. Occasionally, when ECG processing begins (or under extreme noise), the prior QRS complex can become an abnormal beat. This condition may cause all subsequent 'good' beats to be rejected. Hence, one embodiment of the invention includes a mechanism by which the system (or user) can reset the QRS complex. In one variant, the user can reset the ECG rejection model by pressing the system 'Reset' button, or F3 on the keypad (see discussion of apparatus 1400 of FIG. 14 below). This will reset the current QRS after the morphology rejection routine. Alternatively, the system 1400 may be programmed to automatically evaluate and instigate this reset function, with or without warning or indication to the operator (as desired). Various other types of indication and control functions relating to QRS reset may be envisaged by those of ordinary skill provided the present disclosure.

ECG Amplitude—In one embodiment of the invention, an arrhythmia detection algorithm is employed which evaluates the ECG amplitude. For example, at least 100 µV peak-to-peak median amplitude over 4.5 seconds is used in the illustrated embodiments as the basis for ventricular fibrillation detection, although other criteria may be used. This minimum amplitude requirement ensures that electrode disconnection or other hardware failure, which would be monitored as a flat-line ECG trace, is not interpreted as a valid signal. This minimum amplitude translates to a "raw" number (i.e., 26,000) of A/D counts in the exemplary apparatus 1400 of FIG. 14. The raw signal is filtered using high- and low-pass filters that combine to give −26 dB (95% attenuation) in the passband. Based on this filtered output, a minimum amplitude (e.g., 1300 A/D counts) is required for further ECG processing to occur.

Heart Rate—The acceptable heart rate value or range is optionally applied to further evaluate the signals of interest. For example, a minimum or maximum heart rate may be specified, or alternatively an allowable range specified. This criterion (as with others described herein) may be programmatically or systematically varied if desired, such as where the allowable range varies based on user input, or alternatively detected parameters regarding the subject being monitored. In the exemplary embodiment, a nominal range of 40 to 250 bpm is utilized, although other values may be used with equal success.

Arrhythmias—When implemented in an impedance cardiograph monitor or module, the algorithms of the present invention can successfully process data from many patients with cardiac arrhythmias. This provides a significant improvement over the prior art, wherein the monitoring of patients with such arrhythmias was often inaccurate or even impossible.

It is noted that neither AAMI ECAR-1987 nor ANSI/AAMI EC38-1994, which apply to ambulatory cardiographs, provide specific requirements for arrhythmia detection performance. Additionally, AAMI ECAR-1987 considers a detected beat matched with an annotated beat (from the MIT/BIH or AHA databases) if the time between detected and annotated beat is within ±150 msec (±30 samples at a filtered and decimated sample rate of 200 Hz). Exemplary configurations of the algorithms disclosed herein were determined by the Assignee hereof to possess beat detection (pacer spike detection or R point detection) sensitivity≧90% and specificity≧90%, as well as a match detection window much less than the AAMI ECAR-1987 value (i.e., on the order of ±15 samples), thereby providing enhanced ability to monitor arrhythmic patients.

Figure 3:
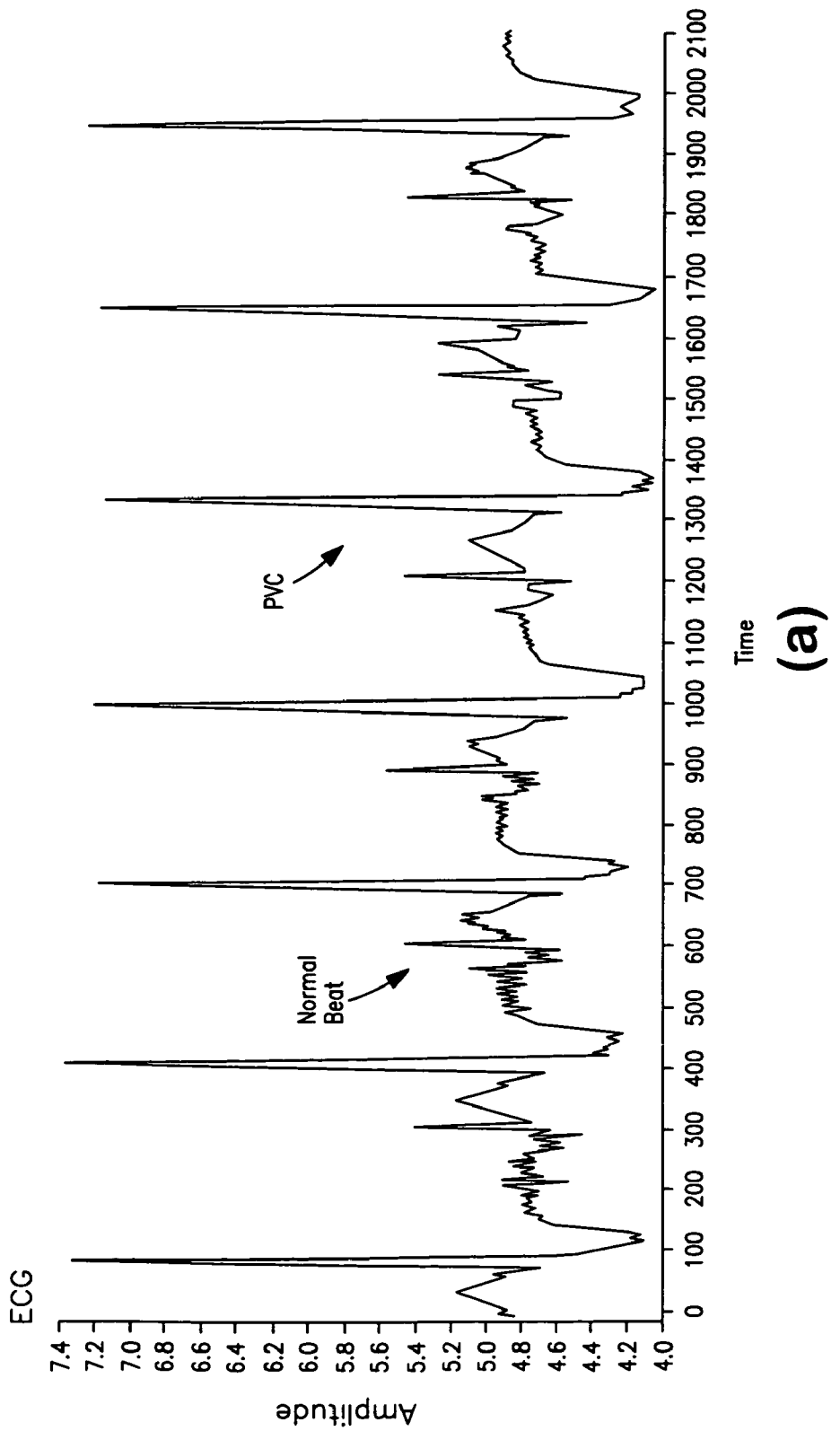
FIG. 3 is a graphical illustration of three ECG arrhythmias.
Figure 3:
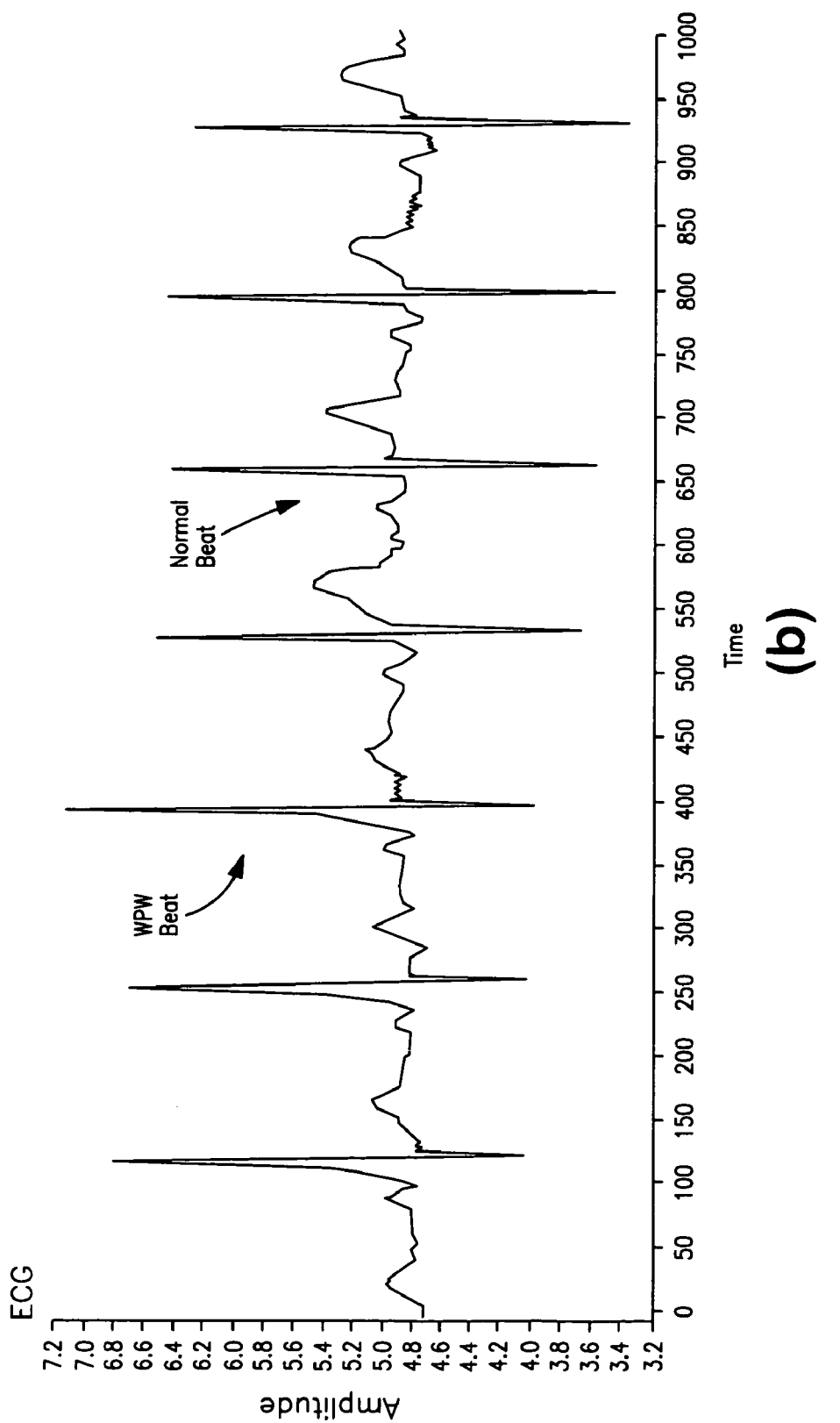
Figure 3:
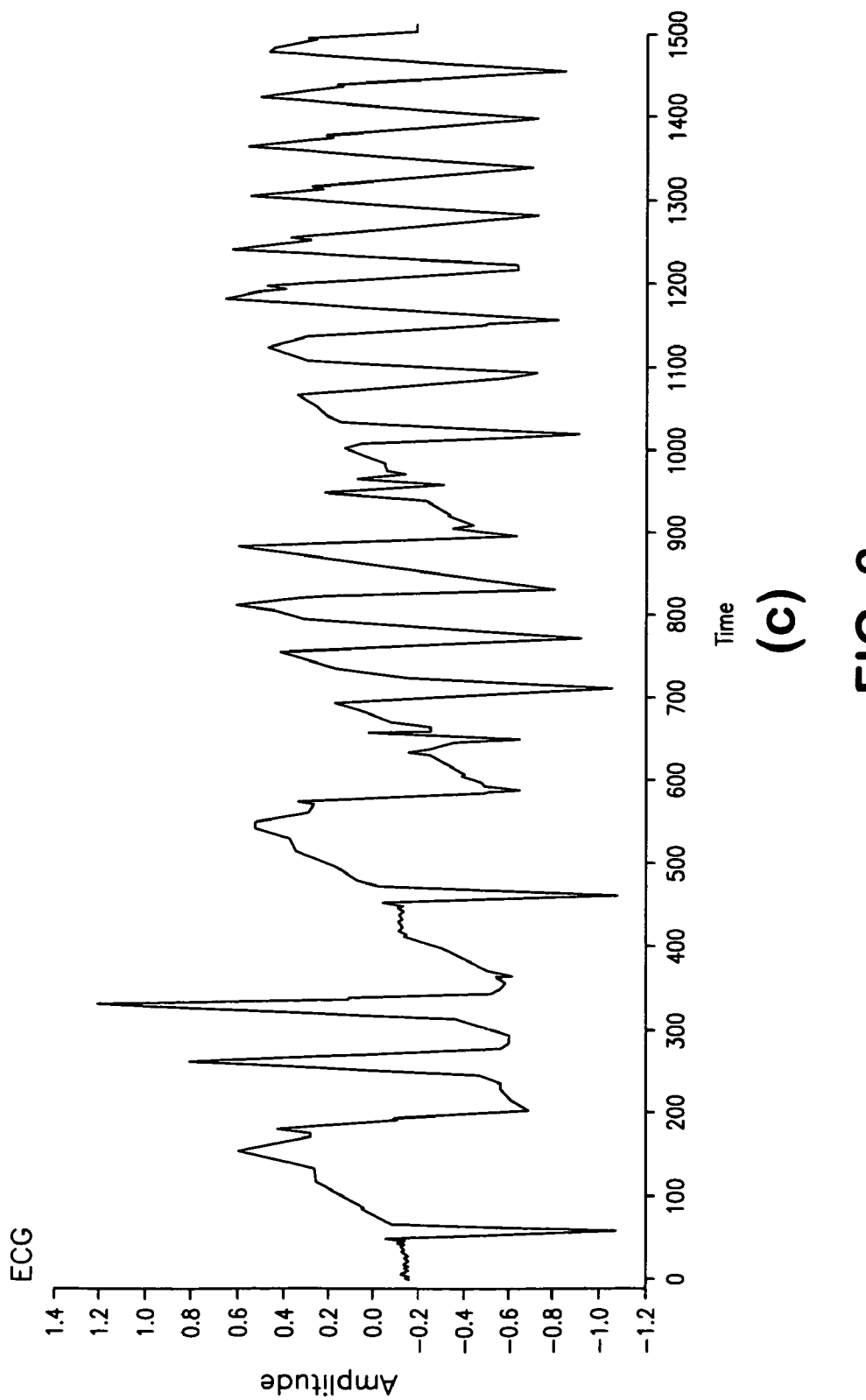

Per AAMI ECAR-1987, flutter and ventricular fibrillation are excluded from summary statistics. Wolff-Parkinson-White syndrome, which results in several QRS morphologies in the same patient, is also excluded from summary statistics. The incidence of Wolff-Parkinson-White (WPW) syndrome is on the order of 0.1 to 0.3% of the general population. Waveforms possessing approximately equal percentages of two morphologies, such as bigeminy, are also excluded from summary statistics. Examples of these arrhythmias are shown in FIG. 3. FIG. 3(*a*) is an example of bigeminy, where every other beat is a premature ventricular contraction (PVC). FIG. 3(*b*) shows a patient traversing from WPW into normal sinus rhythm. FIG. 3*c* is an example of ventricular flutter.

Hence, in the exemplary embodiment of the invention, arrhythmias such as the three shown in FIG. 3 can either be (i) processed by the algorithms described herein (i.e., these algorithms are robust enough to allow such processing without significant degradation), or (ii) optionally excluded from monitoring, such as by visual inspection of the monitor display.

Figure 4:
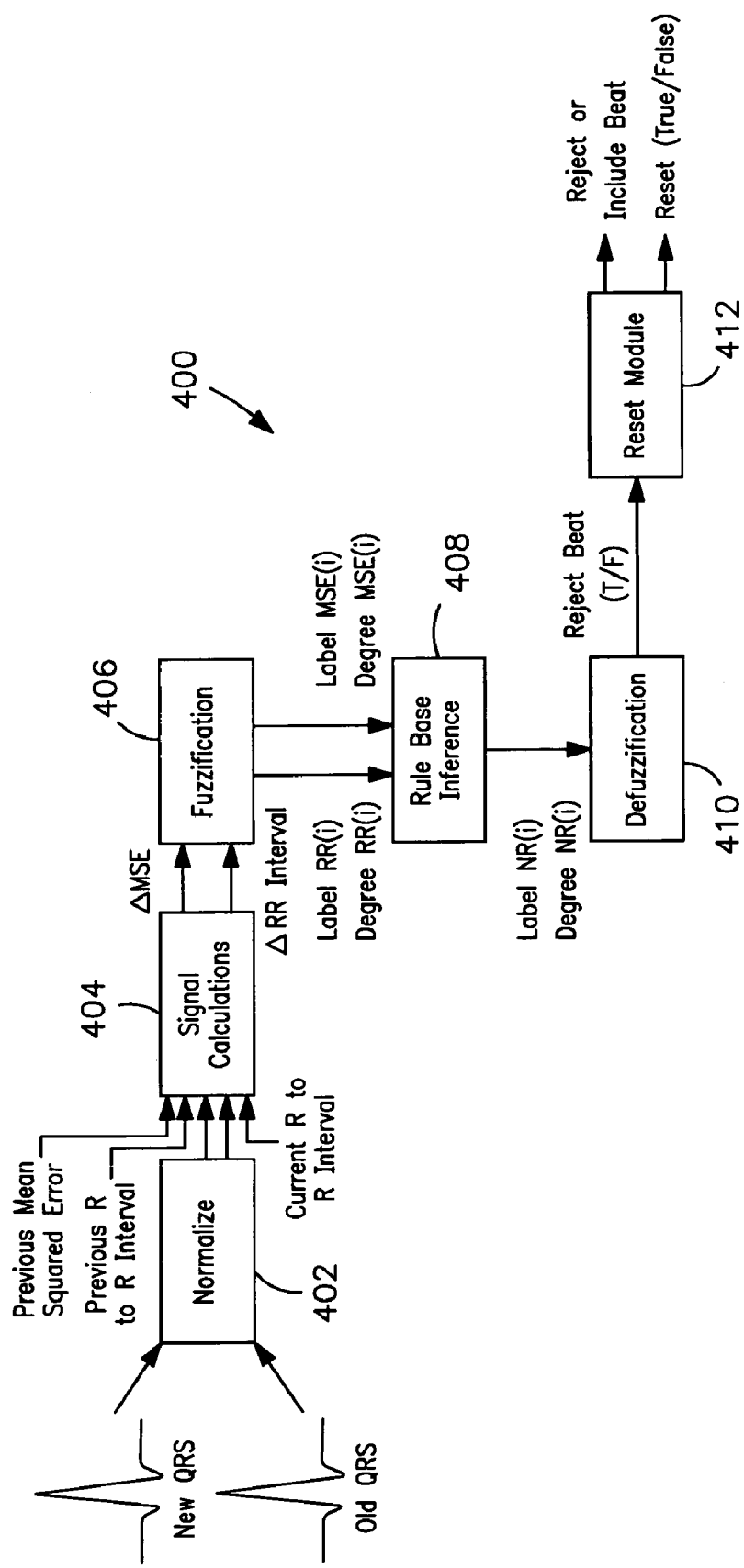
FIG. 4 is a logical block diagram illustrating one exemplary embodiment of the ECG noise (fuzzy) rejection processing according to the invention.

ECG Noise Rejection—In the illustrated embodiment, once a QRS complex is detected, it is first tested for excessive noise using an ECG noise rejection fuzzy model (see step 212 of FIG. 2). This model uses the change in the R-to-R interval from the previous beat, and the change in mean squared error (MSE) from the last n (e.g., n=2) good beats, to determine whether the beat under analysis should be further processed. FIG. 4 illustrates this process 400 graphically.

As shown in FIG. 4, the new and old QRS complexes are first input to a normalization process (step 402). After normalization, a number of different signal calculations are performed (step 404). Inputs to this calculation process include (i) the current R-R interval; (ii) the output of the normalization process 402; the previous R-R interval; and (iv) the previous MSE value. The signal calculation process generates differential (delta) MSE and R-R values, which are then input to a fuzzification process (step 406). The outputs of the fuzzification process 406 are input to rule base inference process (step 408), followed by a defuzzification process (step 410). The output of the defuzzification process (a signal relating to whether the beat should be rejected or not) is then input to a reset module (step 412) that either rejects or includes the new beat.

The normalization of the new and old QRS complexes (step 402) normalizes these complexes to values between 0 and 1, although other normalization schemes or scales may be used. Input parameters to this exemplary process 402 comprise:

1) NewQRS(k)—A predetermined number (e.g., 80) samples around the R point location comprising the current QRS complex; and
2) OldQRS(k)—A predetermined number (e.g., 80) samples around the last R point comprising the last accepted QRS complex.

Output parameters of this process 402 comprise:
1) norm_NewQRS(k)—The QRS complex normalized by the peak to peak amplitude of the original QRS complex; and
2) norm_OldQRS(k)—The QRS complex normalized by the peak to peak amplitude of the original QRS complex.

Input parameters to the illustrated signals calculation process (step 404) of FIG. 4 comprise:
1) norm_NewQRS(k)—The QRS complex normalized by the peak to peak amplitude of the original QRS complex.
2) norm_OldQRS(k)—The QRS complex normalized by the peak to peak amplitude of the original QRS complex.

3) R2RInt_new—The number of samples from the previous R point to the current R Point
4) R2RInt_last—The number of samples from the R point from second to last QRS complex to the R point of the previous QRS complex
5) MSE(m−1)—The mean squared error from the previous good beat where m ∈[0, ..., M], M+1=number of QRS complexes.

Figure 5:
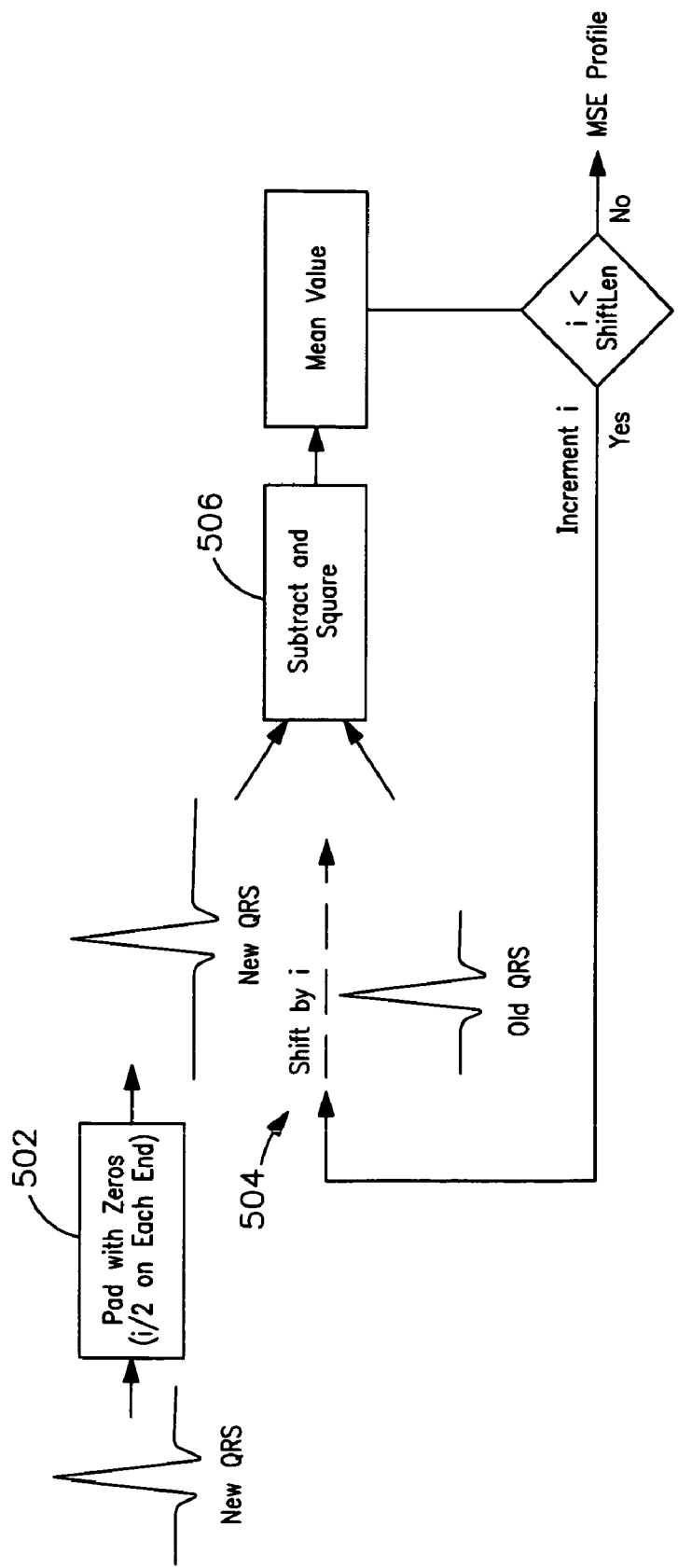
FIG. 5 is a logical block diagram illustrating one exemplary embodiment of the process of creating the mean squared error (MSE) profile within the ECG noise processing of FIG. 4.

Internal Processing of the signal calculation process 404 comprises determining the mean squared error array of the previous and current normalized QRS complexes (MSE_Profile(k)). The mean squared error array (MSE_Profile(k)) is a vector of mean values representing the difference between the two filtered QRS complexes, as the old QRS complex is shifted relative to the new complex (see FIG. 5). As shown in FIG. 5, the new QRS complex is padded with i/2 zeros on each end (step 502), and then shifted or pushed a given amount (i) relative to the old QRS complex (step 504). The new and old QRS complexes are then subtracted and squared (step 506) to obtain a mean value. If the index i is less than a designated value (Shiftlen), then it is incremented and steps 502 through 506 repeated until Shiftlen is reached, at which the MSE_Profile is generated.

The MSE array is constructed using the following exemplary pseudocode algorithm:

```
shift_length = 20;
newqrs_x = mean (norm_NewQRS);
oldqrs_x = mean (norm_OldQRS);
i=0;
if(i<80){
    new_qrs_nomean(i) = norm_NewQRS(i) − newqrs_x;
    old_qrs_nomean(i) = norm_OldQRS(i) − oldqrs_x;
    i++;}
zeros_array=CREATEARRAY(0, 10)
/*create an array of zeros with length of 10*/
long_new_qrs= CONCATENATEARRAYS(zeros_array,
new_qrs_nomean,
zeros_array);
j=0;
FOR(j<20){
    subs_long_qrs = long_old_qrs(j:80) /*take a 80 sample subset from j forward*/
    difference = subs_long_qrs − old_qrs_nomean;
    square = difference * difference;
    MSE_profile_raw(j) = MEAN(square);
    j++;}
MSE_Profile = 1000*(MSE_profile_raw)
/*Normalize the MSE array by the max value and multiply by 100 */
```

The mean squared error array of the current QRS complex comprises the minimum value from the MSE_Profile array, and is calculated using the relationship of Eqn (6) below:

$$MSE = \begin{cases} 1 & \min[MSE\_Profile(k)] \leq 1 \\ \min[MSE\_Profile(k)] & \text{otherwise} \end{cases} \quad (6)$$

The output parameters of the signal calculation process 404 comprise:
1) ΔMSE—The mean squared error value for the two given QRS complexes. This value is expressed as a fractional change, and may be calculated according to Eqn. (7) below:

$$\Delta MSE = \text{abs}\left\{\frac{[MSE(m) - MSE(m-1)]}{MSE(m-1)}\right\}, \quad (7)$$

where m ∈[0, ..., M], M+1=number of QRS complexes

2) ΔRR—The R point-to-R point interval change between the current and previous QRS complexes. This value is, in the current embodiment, expressed as a fractional change, and is calculated according to Eqn. (8) below:

$$\Delta RR = \text{abs}\left\{\frac{(RR(m) - RR(m-1))}{RR(m-1)}\right\}, \quad (8)$$

where $m \in [0, ..., M]$, $M+1$ = number of QRS complexes

Fuzzification—The "crisp" inputs are, in the illustrated embodiment of FIG. 4, translated through membership functions into a plurality of fuzzy inputs. This process 406 is graphically illustrated in FIG. 6. Input parameters to the fuzzification process (i.e., to produce the fuzzy inputs for the rule base inference process 408) comprise:
1) ΔMSE—The mean squared error value for the two given QRS complexes; and
2) ΔRR—The R point to R point interval change between the current and previous QRS complexes.

Figure 6:
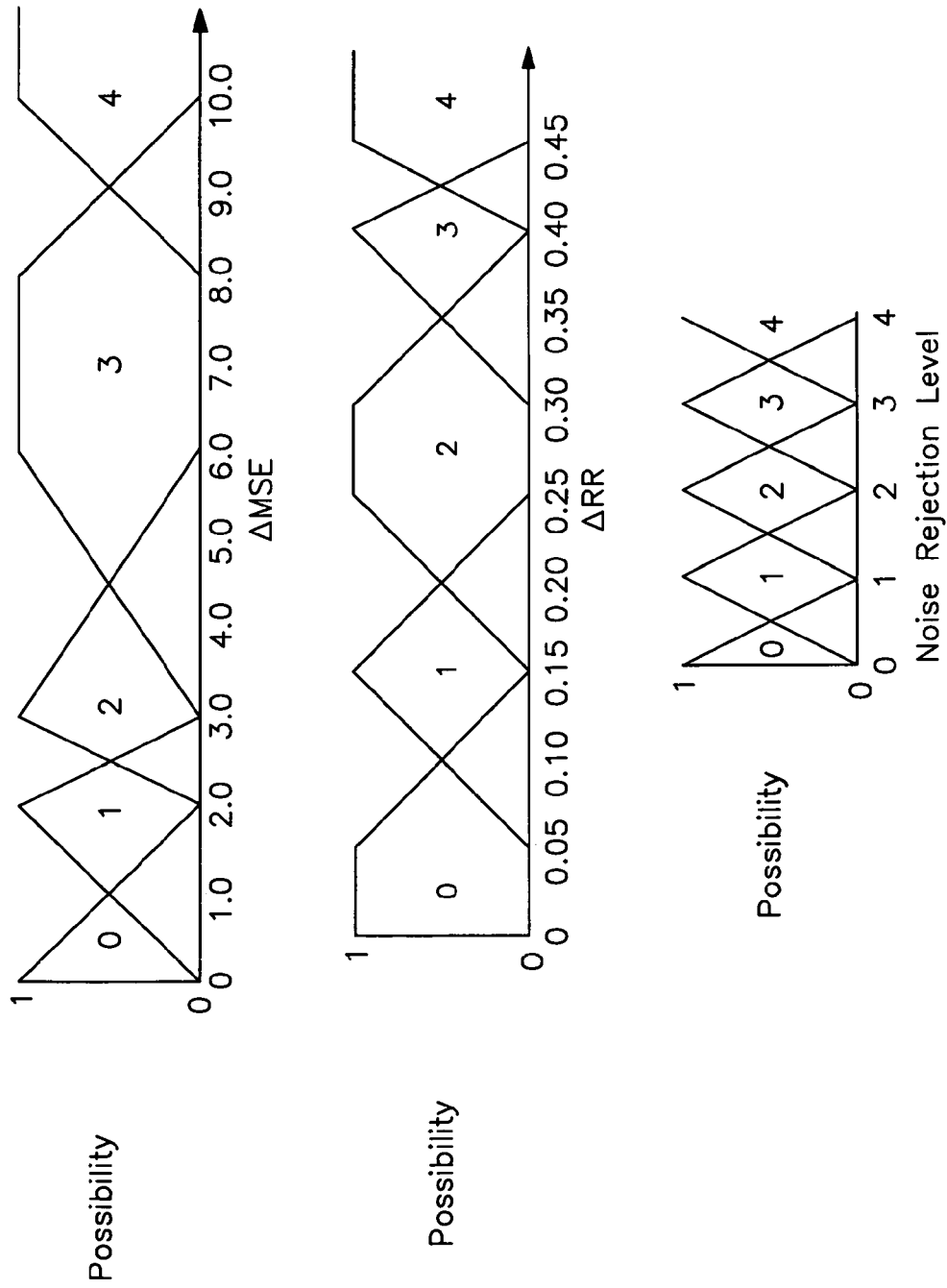
FIG. 6 is a graphical representation of exemplary input membership functions for MSE and the R-to-R interval change, and output membership functions for the fuzzy noise rejection processing of FIG. 4.

Internal processing conducted by the fuzzification process 406 of FIG. 6 comprises:
1) M_mse—Low resolution mean squared error change. M_mse is calculated according to Eqn. (9):

$M\_mse(m)$=ROUND($\Delta MSE(m)$), where M_mse is bounded within the range {0,10}. (9)

2) M_rr—Low resolution R to R interval. M_rr may be calculated according to Eqn. (10):

$M\_rr(m)$=INT($\Delta RR(m)$/0.05)+ROUND[MOD($\Delta RR(m)$/0.05)/0.05]where M_rr is bounded within the range {0,9}. (10)

Output parameters of the aforementioned exemplary fuzzification process 406 comprise:
1) LabelRR(i)—One or two labels associated with M_rr, based on Table 1 (Appendix A).
2) DegreeRR(i)—Degree associated with each M_rr label, based on Table 2 (Appendix A).
3) LabelMSE(i)—One or two labels associated with M_mse, based on Table 3 (Appendix A).
4) DegreeMSE(i)—Degree associated with each M_mse label, based on Table 4 (Appendix A).

Rule Based Inference—The fuzzy inputs to the rule base inference process 408 (i.e., the outputs of the fuzzification process 406) are processed using a Zadeh intersection approach (or other comparable process) in order to obtain the fuzzy outputs. The input parameters comprise elements 1)-4) shown above, and the output parameters comprise:
1) LabelNR(i)—One to four labels associated with RejectionLevel. Each combination of LabelRR(i) and LabelMSE(i) is input to a structure such as that of Table 5 (Appendix I) to determine LabelNR(i).
2) DegreeNR(i)—Degree associated with each RejectionLevel label. For each combination of LabelRR(i) and LabelMSE(i), the minimum associated DegreeRR(i) or DegreeMSE(i) is output as DegreeNR(i).

Defuzzification—As part of the defuzzification process 410 of the illustrated embodiment of FIG. 4, the fuzzy outputs are processed back to a crisp output using the well known centroid method, although other defuzzification methods may be used consistent with the invention. Input parameters to the defuzzification process include LabelNR(i) and DegreeNR(i) described above, as well as MF(i,j) (membership functions for NoiseRejectionLevel). The row index (i) of MF(i,j) represents e.g., the label 0-4. The column index (j) represents the membership function sample. Table 6 (Appendix I) shows an exemplary membership function array configuration. Internal processing of the defuzzification process 410 comprises:

1) F(j)—Fuzzification union. The union of the individual membership functions, with associated degrees, is taken according to Eqn. (11):

$$F(j)=\text{clip}\{\text{Degree}N(0), MF[\text{Label}N(0),:]\}\cup\text{clip}\{\text{Degree}N(1), MF[\text{Label}N(1),:]\}\cup\text{clip}\{\text{Degree}N(2), MF[\text{Label}N(2),:]\}\cup\text{clip}\{\text{Degree}N(3), MF[\text{Label}N(3),:]\} \quad (11)$$

where the notation ":" refers to using all indices e.g., j=0 to 4, and clip[x,y(j)] refers to clipping all values of the function y(j) at the maximum value of x.

2) RejectionLevel—The noise class is found from calculating the centroid of the fuzzification union as in Eqn. (12):

$$RejectionLevel = \frac{\sum_{j=0}^{4} F(j) \cdot (j)}{\sum_{j=0}^{4} F(j)} \quad (12)$$

Output parameters of the exemplary defuzzification process 410 of FIG. 4 comprise:

1) RejectBeatN—Boolean value representing whether the beat is noisy or not. The value is set to true if RejectionLevel is greater than or equal to a predetermined value (e.g. 2).

Figure 7:
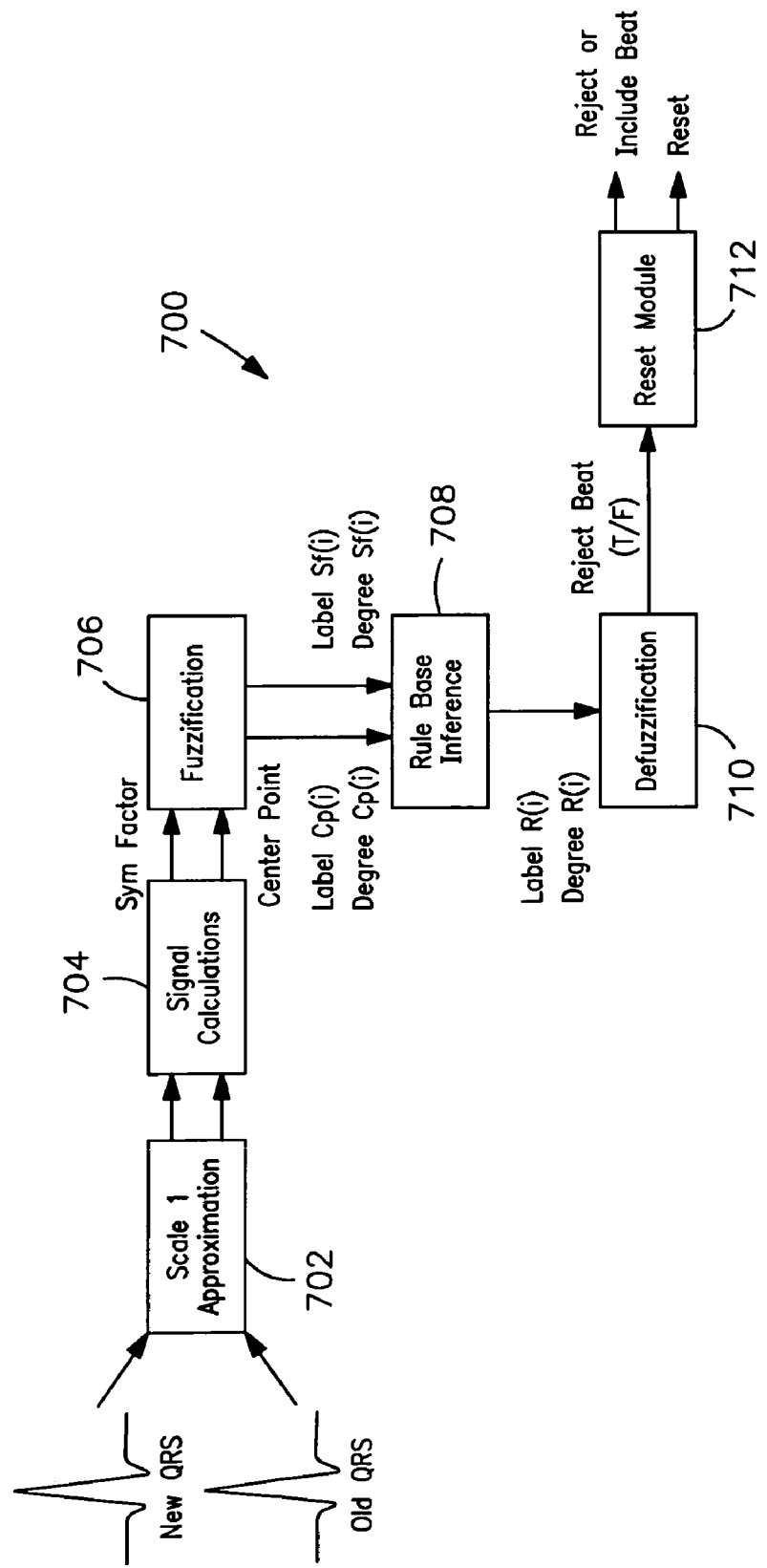
FIG. 7 is a logical block diagram illustrating one exemplary embodiment of the ECG morphology (fuzzy) rejection processing according to the invention.

ECG Morphology—The morphology, or shape, of the ECG is also used in the exemplary process of FIG. 2 to reject dissimilar beats (see step 216). Each incoming QRS complex is compared to a previous QRS complex (e.g., the QRS immediately preceding the current complex being evaluated), and a fuzzy model determines whether to include or reject a beat. FIG. 7 graphically illustrates this process 700.

As shown in FIG. 7, a process generally comparable to that of FIG. 4 is performed for morphology testing, with the exception that a Scale 1 approximation process (step 702) is first performed on the new and old QRS complexes. The outputs of this process 702 are then input to a signal calculation process (step 704), which is followed by fuzzification (step 706), rule base inference (step 708), and defuzzification (step 710).

The Scale 1 wavelet filter process, to obtain wavelet transform approximation coefficients 702 of FIG. 7, may take any number of different forms. In one exemplary variant, the filter is calculated based on a reverse biorthogonal 2.2 wavelet of the type well known in the signal processing arts. Other wavelet (and even non-wavelet) filtering approaches may also be used consistent with the invention. This same wavelet filter may advantageously also be used if desired for other functions, such as e.g., X point detection. Input parameters for the exemplary Scale 1 filtering process 702 of FIG. 7 comprise:

1) NewQRS(k)—N (e.g., 80) samples around the R point location comprising the current QRS complex;
2) OldQRS(k)—N (e.g., 80) samples around the last R point comprising the last accepted QRS complex; and
3) bH0 to bH32—Exemplary reverse biorthogonal 2.2 wavelet filter coefficients are listed in Table 7 of Appendix I.

Output parameters of the exemplary Scale 1 filter process 702 comprise:

1) S1_NewQRS(k)—samples comprising the wavelet filtered Scale 1 approximation of the current QRS complex using the standard convolution; and
2) S1_OldQRS(k)—samples comprising the wavelet filtered Scale 1 approximation of the last accepted QRS complex using the standard convolution.

Signal Calculations—Input parameters for the signal calculation function 704 of FIG. 7 include:

1) S1_NewQRS(k)—samples comprising the scale 1 approximation of the current QRS complex; and
2) S1_OldQRS(k)—samples comprising the scale 1 approximation of the last accepted QRS complex.

Internal processing for the signal calculation function 704 includes determination of MSE_Profile(k), or the mean squared error array of the previous and current QRS complex. The mean squared error profile of the illustrated embodiment is a vector of mean values representing the difference between the two filtered QRS complexes, as the old QRS complex is iteratively shifted relative to the new complex. This process was previously described with respect to FIG. 5, and is completely analogous in the context of the present morphology analysis.

For morphology rejection, the exemplary value of the shift length is 120 samples, and traverses the full length of both signals. It will be recognized, however, that other lengths may be used, and in fact other types of processes.

The following exemplary pseudocode illustrates one possible construction algorithm for the MSE array:

```
shift_length = 120;
newqrs_x = mean (S1_NewQRS);
oldqrs_x = mean (S1_OldQRS);
i=0;
if(i<40){
    new_qrs_nomean(i) = S1_NewQRS(i) - newqrs_x;
    old_qrs_nomean(i) = S1_OldQRS(i) - oldqrs_x;
    i++;}
zeros_array=CREATEARRAY(0, 40) /*create an array of zeros with length of 40*/ long_old_qrs=
CONCATENATEARRAYS(zeros_array,
old_qrs_nomean, zeros_array);
j=0;
long_mean_array = CREATEARRAY(0,shiftlength);
FOR(j<80){
    subs_long_qrs = long_old_qrs(j:40)
    /*take a 40 sample subset from j forward*/
    difference = subs_long_qrs - new_qrs_nomean;
    square = difference * difference;
    long_mean_array(j) = MEAN(square);
    j++;}
MSE_profile_raw = long_mean_array(10:70);
MSE_Profile = 100*(MSE_profile_raw/MAX(MSE_Profile_raw))
/*Normalize the MSE array by the max value and multiply by 100 */
```

The following values are also defined in the signals calculation process 704:
1) Cp_y—The y axis value of the minimum point of MSE_profile.
2) Cp_x—The x axis value of the minimum point of MSE_profile.
3) Leftmax—Beginning at Cp_x and decrementing by one sample in MSE_profile, find the first sample that satisfies Eqn. (13):

$$MSE\_Profile(k-1) < MSE\_Profile(k) \quad (13)$$

4) Rightmax—Beginning at Cp_x and incrementing by one sample in MSE_profile, find the first sample that satisfies Eqn. (14):

$$MSE\_Profile(k+1) < MSE\_Profile(k) \quad (14)$$

Figure 9:
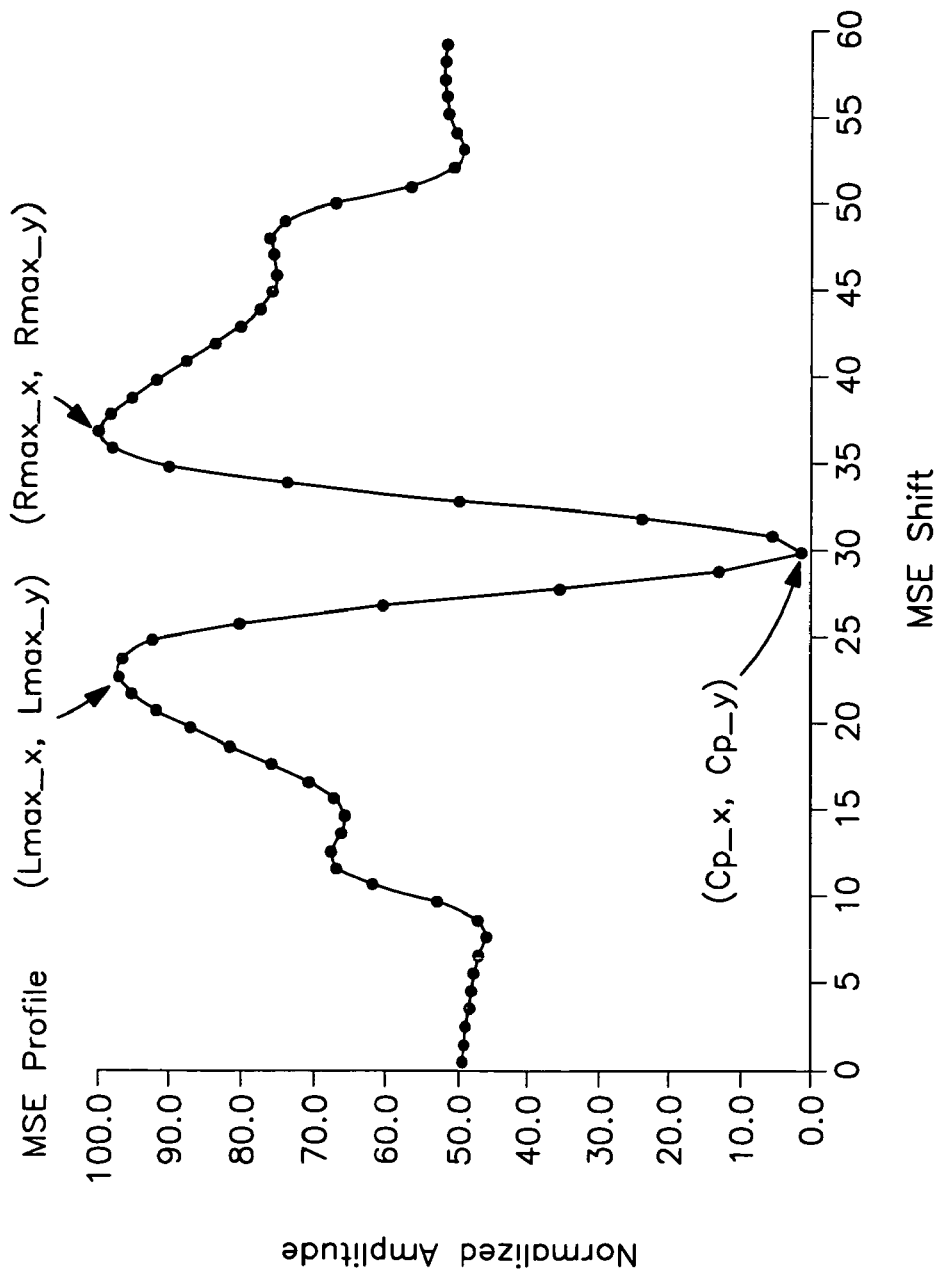
FIG. 9 is a graphical representation of an exemplary mean squared error (MSE) profile, including points used to determine the morphology similarity.

5) Rmax_x—The x axis value of the Rightmax location (see FIG. 9).
6) Rmax_y—The y axis value of the Rightmax location.
7) Lmax_x—The x axis value of the Leftmax location.
8) Lmax_y—The y axis value of the Leftmax location.

Exemplary output parameters for the signal calculation function 704 of FIG. 7 comprise:
1) SymFactor—The symmetry factor for the MSE_Profile array are calculated according to Eqn. (15):

$$SymFactor = Cp\_y + abs((Rmax\_x - Cp\_x) - (Lmax\_x - Cp\_x)) + abs(Rmax\_y - Lmax\_y) \quad (15)$$

2) CenterPoint—The x axis location of the minimum of the MSE_Profile array, Cp_x.

Figure 8:
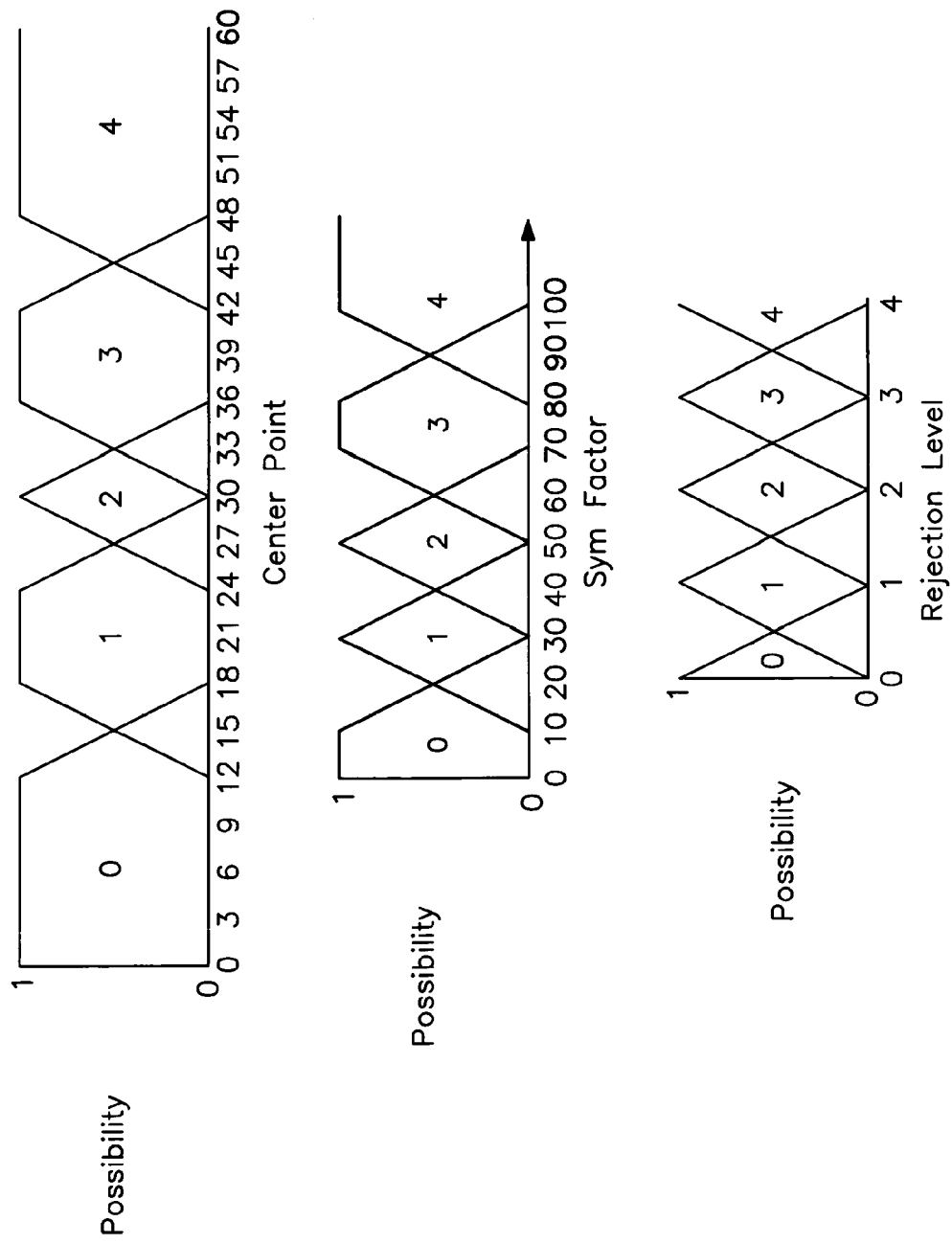
FIG. 8 is a graphical representation of exemplary input and output membership functions for the fuzzy morphology processing of FIG. 7.

Fuzzification—As shown in the exemplary process 700 of FIG. 7, the crisp inputs are translated through membership functions into fuzzy inputs via a fuzzification process 706. Input parameters to this process 706 comprise SymFactor and CenterPoint defined above. FIG. 8 illustrates exemplary input membership functions for CenterPoint and SymFactor, and output membership functions for RejectionLevel.

Internal processing performed by the exemplary fuzzification process 706 of FIG. 7 includes:
1) Mcenterpt—Low resolution center point. Mcenterpt is calculated according to Eqn. (16):

$$Mcenterpt = INT(CenterPoint/3) + ROUND[MOD(CenterPoint/3)/3] \quad (16)$$

where Mcenterpt is bounded within a predetermined range; e.g., $\{0,16\}$.

2) Msymfact—Low resolution symmetry factor. Msymfact is calculated according to Eqn. (17):

$$Msymfact = INT(SymFactor/10) + ROUND[MOD(SymFactor/10)/10] \quad (17)$$

where Msymfact is bounded within the range $\{0,10\}$.

Exemplary output parameters of the fuzzification process 706 of FIG. 7 include:
1) LabelCp(i)—One or two labels associated with Mcenterpt, based on Table 8 of Appendix I.
2) DegreeCp(i)—Degree associated with each Mcenterpt label, based on Table 9 of Appendix I.
3) LabelSf(i)—One or two labels associated with Msymfactor, based on Table 10 of Appendix I.
4) DegreeSf(i)—Degree associated with each Msymfactor label, based on Table 11 of Appendix I.

Rule Base Inference—In the exemplary methodology of FIG. 7, the fuzzy inputs are processed using a rule based inference process 708 (the Zadeh intersection in the illustrated embodiment) to obtain fuzzy outputs. Exemplary input parameters to this process 708 comprise the output parameters 1)-4) of the fuzzification process 706 listed above. Output parameters of the rule based inference process 708 comprise:
1) LabelR(i)—One to four labels associated with RejectionLevel; and
2) DegreeR(i)—Degree associated with each RejectionLevel label.

Each combination of LabelCp(i) and LabelSf(i) are input to Table 12 (Appendix I) to determine LabelN(i). For each combination of LabelCp(i) and LabelSf(i), the minimum associated DegreeCp(i) or DegreeSf(i) are output as DegreeR(i).

Defuzzification—The fuzzy outputs of the rule base inference process 708 are processed to one or more crisp outputs using, e.g., the centroid or other comparable method. Input parameters to this defuzzification process 710 comprise: 1) LabelR(i)—One to four labels associated with RejectionLevel; 2) DegreeR(i)—Degree associated with each RejectionLevel label; and 3) MF(i,j)—Membership functions for RejectionLevel.

For MF(i,j), the row index (i) represents the label 0-4. The column represents the membership function sample. This array is shown in Table 13 of Appendix I.

Internal processing conducted by the exemplary defuzzification process 710 comprises determination of the Fuzzification union F(j). This variable comprises the union of the individual membership functions, with associated degrees, is taken as shown in Eqn. (18):

$$F(j) = \text{clip}\{DegreeN(0), MF[LabelN(0),:]\} \cup \text{clip}\{DegreeN(1), MF[LabelN(1),:]\} \cup \text{clip}\{DegreeN(2), MF[LabelN(2),:]\} \cup \text{clip}\{DegreeN(3), MF[LabelN(3),:]\} \quad (18)$$

where the notation ":" refers to using all indices j=0 to 4 and clip[x,y(j)] refers to clipping all values of the function y(j) at the maximum value of x.

Internal processing conducted by the exemplary defuzzification process 710 also comprises determination of the RejectionLevel variable; i.e., the noise class is found from calculating the centroid of the fuzzification union as shown in Eqn. (19):

$$RejectionLevel = \frac{\sum_{j=0}^{4} F(j) \cdot (j)}{\sum_{j=0}^{4} F(j)} \quad (19)$$

Exemplary output parameters from the defuzzification process 710 comprise RejectBeatM, the Boolean value representing in the present embodiment whether the beat is noisy or not. The value is set to "true" if RejectionLevel meets a designated criterion; e.g., is greater than or equal to a predetermined value such as 2.

Reset Module—The reset module 712 of the process 700 of FIG. 7 is designed to be an intelligent means for resetting the ECG morphology model without the need for user input. In the illustrated embodiment, if either of the beat rejection models (e.g., ECG noise or morphology) determines that a beat should be rejected, the beat will optionally be passed through the reset module 712. The reset module tests against one or more conditions that can aid in determining whether there are conditions occurring within the input vectors (i.e., ECG source leads and associated signals) or the noise/morphology process itself that are undesirable or otherwise indicative of a less-than-optimal condition. For example, as shown in the exemplary decision flow of FIG. 10, these one or more conditions comprise: (i) whether or not the beat is rejected 1002; (ii) whether n (e.g., n=5) consecutive rejections have occurred 1004; (iii) whether a predetermined number (e.g., two) or more previous resets of the ECG module have occurred 1006; (iv) whether an automatic ECG vector determination has already been performed 1008; and (v) whether a predetermined period of time has elapsed (e.g., 30 seconds) 1010.

The first condition 1002 is used to pre-screen for only rejected beats (i.e., those that are rightfully analyzed via the reset module). The second condition 1004 is used to determine if a series of beats are being rejected, such as where each beat is defective or otherwise unsuitable in some fashion (e.g., very low amplitude or other undesirable characteristics).

The third condition 1006 is used to determine whether (another) ECG module reset is warranted (i.e., identifying where prior resets have not cured the deficiency).

The fourth condition 1008 is used to determine whether a prior ECG vector automatic selection has been performed.

Finally, the fifth condition 1010 is used to prevent an error message being issued where a predetermined elapsed time (e.g., 30 seconds) has not yet elapsed.

If all of these conditions are met, the system enters an error state, and generates a display and/or audible error message, such as e.g., "Unable to acquire ECG. Perform System Test to verify system integrity. Contact Technical Support if System Test fails."

Input parameters to the reset module process 712 comprise: 1) RejectBeat, a Boolean value representing whether the beat is noisy or not, that is set by either the morphology or noise rejection models; 2) PastRejectionArray, an array containing the Boolean rejection values for the past n (e.g., 4) detected beats; 3) ResetCount, a counter for the number of consecutive resets; 4) AutoECG, a Boolean value set to false at the beginning of a session (if the AutoECG algorithm is performed during the current session, it is set to true); and 5) Timer, a seconds counter that is initialized at the completion of AutoECG. The counter runs from 0 to 30s in the illustrated embodiment, although other initiation points and durations may be utilized.

Internal processing of the exemplary embodiment of the reset module comprises processing according to the following algorithm. This algorithm is graphically illustrated in FIG. 10, previously discussed herein.

```
RejectBeat; /* Boolean Value */
PastRejectionArray; /* Array of 4 Boolean values */
ResetCount; /* Counter for ECG model resets */
AutoECG; /* Boolean value */
Timer; /* Time in seconds following an AutoECG lead selection */
If(RejectBeat){
   Consec_rej = SUM(PastRejectionArray);
   /*Using the numerical equivalent of True/False add up the number of
   true values in the array, 4 indicates the need for a Reset (the current
   beat makes beat makes the 5th consecutive*/
   If(Consec_rej = 4){
      If(ResetCount = 2){
         If(AutoECG){
            If(Timer < 30s){
               ResetECGModel;
               /* Drop the current ECG morphology and get
               the next beat as the new model for
               comparison */
               ResetCount = ResetCount + 1;
               PastRejectionArray = [ ]; /*Empty the
               array*/
            } else {
               DISPLAYERROR("Unable to acquire ECG.
               Perform System Test to verify system
               integrity. Contact Technical Support if
               System Test fails.");
            }
         } else {
            AUTO_ECG_ALGORITHM;
            /* Run the automatic ECG selection algorithm, and
            switch to the given lead */
            AutoECG = True;
            START_TIMER(Timer);
            /* Start Timer when AutoECG has finished */
         }
      } else {
         ResetECGModel;
         PastRejectionArray = [ ]; /*Empty the array*/
         ResetCount = ResetCount + 1;
      }
   } else {
      REJECT_BEAT;
      /* Reject the beat and continue processing the ECG data */
      PastRejectionArray = PastRejectionArray[1:4] + RejectBeat;
      /*Drop the oldest beat and add in the new Boolean */
   }
} else {
   /* Do Nothing, continue processing the ECG */
}
```

Output parameters of the exemplary reset module process 712 comprise: (1) PastRejectionArray—Array containing the Boolean rejection values for the past 4 detected beats; (2) ResetCount—Counter for the number of consecutive resets; (3) AutoECG—Boolean value set to false at the beginning of a session; and (4) Timer—time (e.g., seconds) counter that is initialized at the completion of AutoECG.

It is noted that under one implementation of the present invention by the Assignee hereof, the two levels of ECG rejection criteria previously described herein were validated in 464 ECG beats collected from 21 cardiac patients, 13 of whom were not paced. These patient data were not used in algorithm training. An expert user not involved in algorithm training visually labeled each beat as rejected or nonrejected; these labels were used as reference data. During this validation, with "true positive" defined as an ECG beat that was correctly rejected, 98% sensitivity and 96% specificity were obtained, thereby providing experimental verification of the efficacy of this implementation of the present invention.

Delta Z Rejection Criteria

Figure 11:
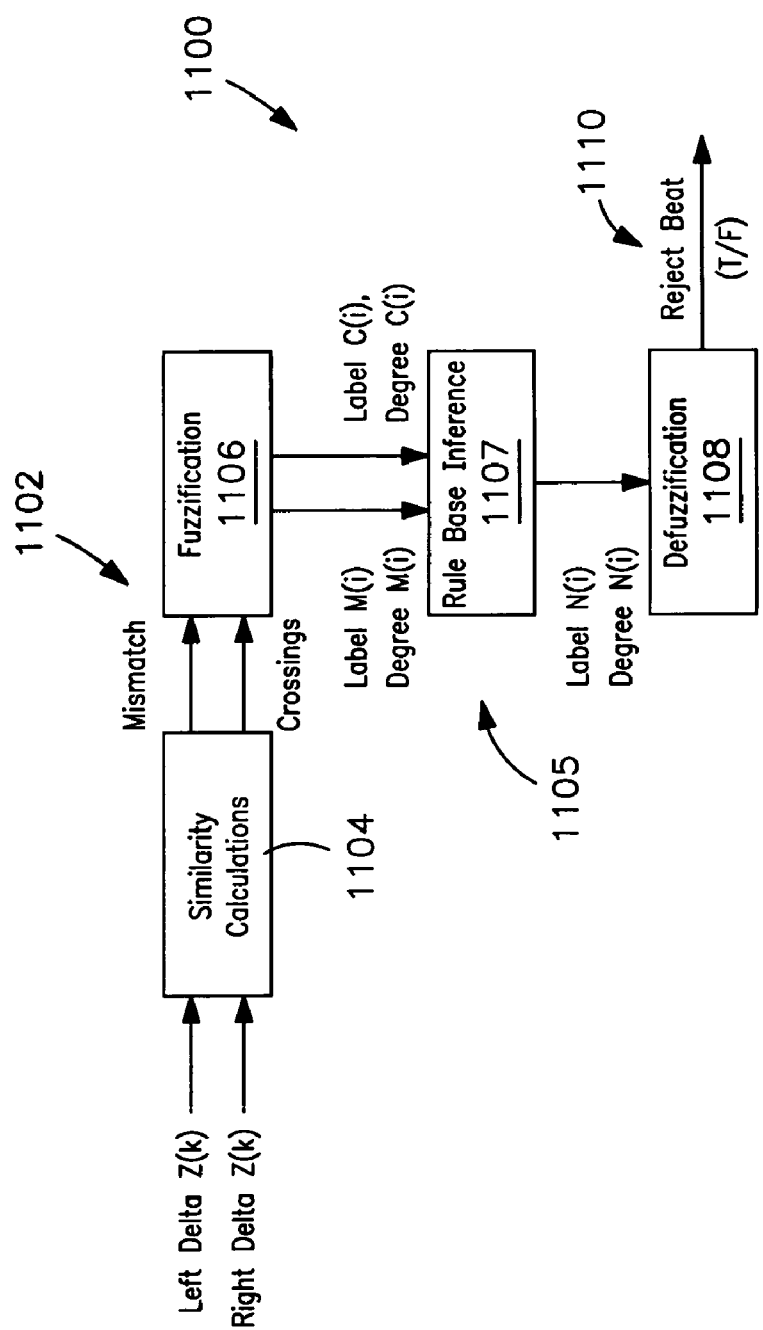
FIG. 11 is a logical block diagram illustrating one exemplary embodiment of the Delta Z (fuzzy) similarity rejection processing according to the invention.
Figure 12:
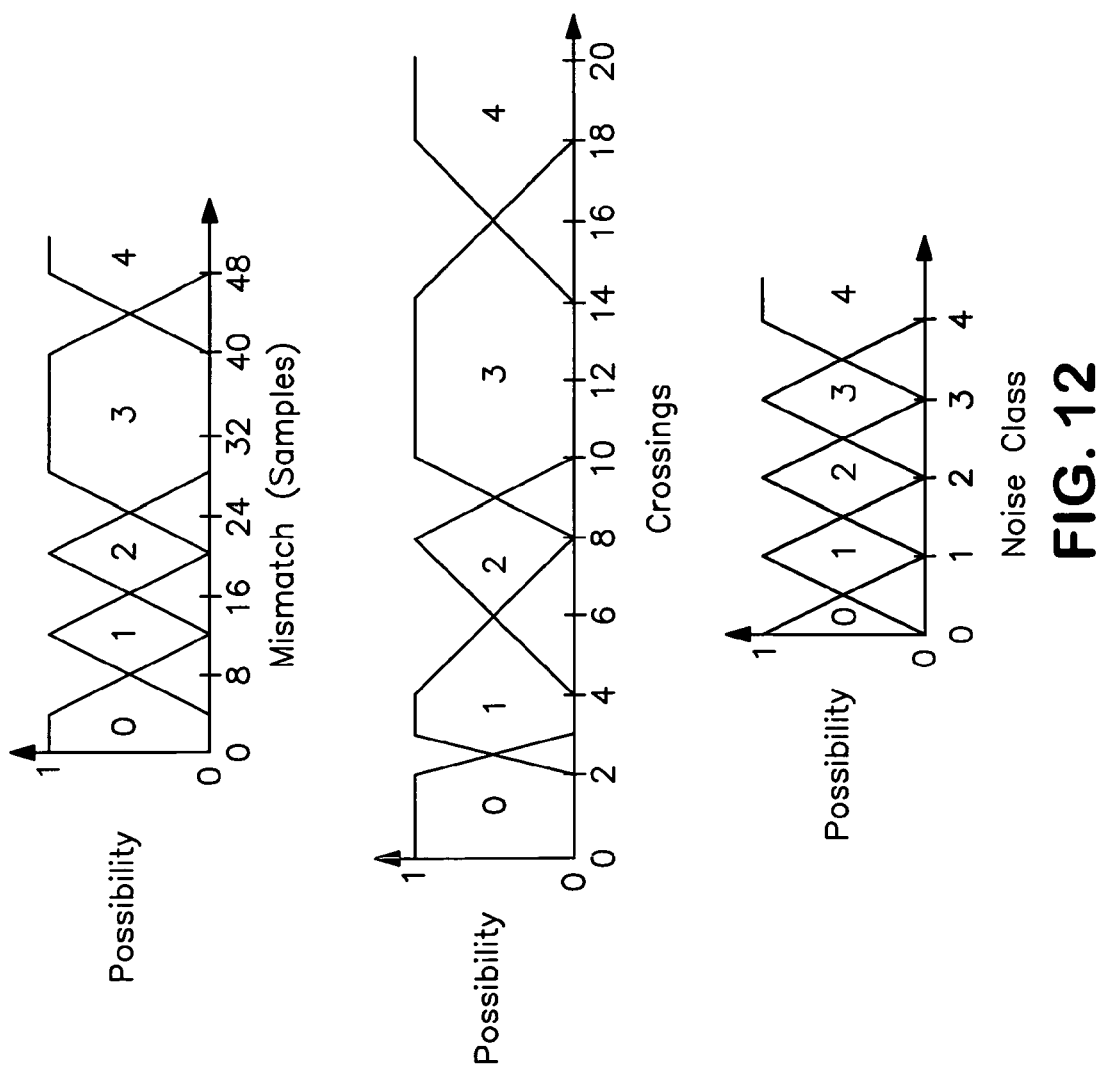
FIG. 12 is a graphical representation of exemplary input and output membership functions for the fuzzy Delta Z similarity processing of FIG. 11.
Figure 13:
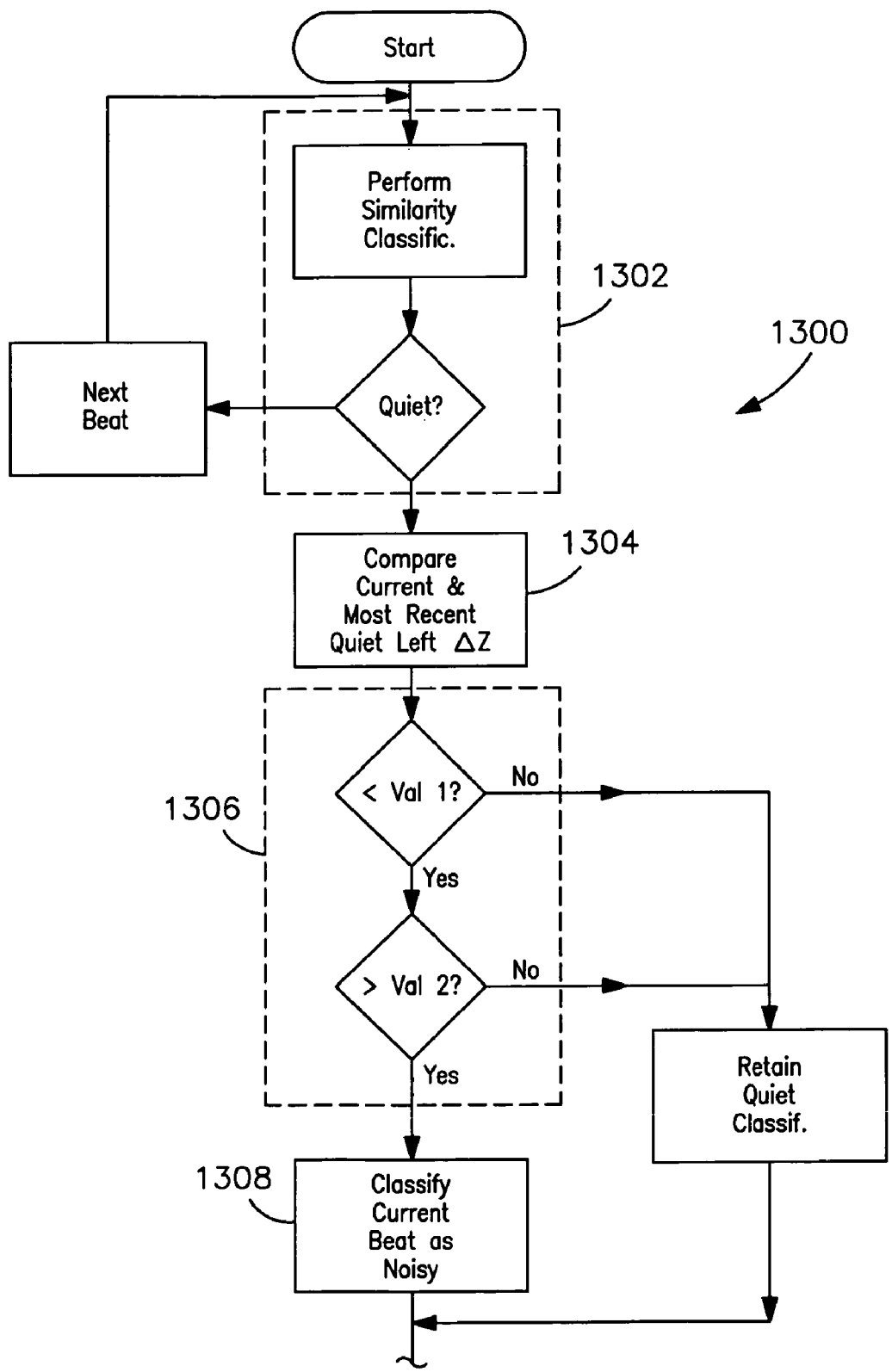
FIG. 13 is a logical flow diagram illustrating one exemplary embodiment of the method of evaluating signals (e.g., Delta Z) for reproducibility according to the invention.

Referring now to FIGS. 11-13, the Delta Z rejection processing according to the exemplary embodiment of the invention is described in detail.

As previously noted with respect to FIG. 1, the Delta Z rejection processing comprises a second tier of the analytical hierarchy. Specifically, in those situations where the ECG can be used to parse Delta Z beats, the following three criteria are used for Delta Z beat rejection at the prescribed frequency (e.g., 200 Hz): (i) Delta Z amplitude; (ii) Delta Z similarity; and (iii) Delta Z reproducibility. These three criteria are now described in greater detail.

(i) In the exemplary embodiment, those Delta Z beats possessing amplitudes<22 mohms may not be processed accurately using empirical detection. With wavelet processing, this minimum acceptable amplitude can be significantly reduced (e.g. to 17 mohms), although it will be recognized that other values may be used consistent with the invention.

Exemplary methods for wavelet processing are described in, inter alia, co-owned U.S. Pat. No. 6,561,986 to Baura, et al. issued May 13, 2003 entitled "Method and apparatus for hemodynamic assessment including fiducial point detection" which is incorporated herein by reference in its entirety.

(ii) When applying the Delta Z similarity criterion, the similarity between left and right Delta Z beats is analyzed to classify "quiet" and "noisy" beats. If a beat is classified as noisy, it is rejected. Classification is made with a fuzzy model, one embodiment of which is illustrated in the exemplary process 1100 of FIG. 11. The inputs 1102 to the fuzzy model comprise the mismatch between the global minimum and maximum of the Haar wavelet transformed normalized left and right beats (Mismatch), and the number of zero crossings between the difference of normalized beats (Crossings). If the left and right beats are similar, then the number of samples between global minima and maxima is small, leading to a small mismatch. If the left and right beats are similar, then several zero crossings will occur in the difference due to random noise. The model output comprises the Boolean value (Reject Beat) 1110. Exemplary input and output membership functions for this model are shown in FIG. 12, although it will be recognized that other may be substituted.

The similarity calculations 1104 of the process 1100 of FIG. 11 enable the calculation of crisp inputs to the fuzzy model 1105. These inputs are transformed through a fuzzification process 1106, which utilizes the input membership functions, into fuzzy inputs. The fuzzy inputs are mapped to fuzzy outputs using rule base inference (RBI) process 1107. Through a defuzzification process 1108, which utilizes the output membership function, the crisp noise class value is determined. In the illustrated embodiment, if the noise class$\geq$2, the beat is considered noisy and is rejected.

Input parameters to the similarity calculations 1104 comprise: (1) LeftDeltaZ(k)—samples comprising one beat of Left DeltaZ(k), from the R point to most recent Q point; if this is a paced beat, the Q to R interval is assumed to be N (e.g., 6) samples; and (2) RightDeltaZ(k)—samples comprising one beat of Right DeltaZ(k), from the R point to most recent Q point; if this is a paced beat, the Q to R interval is assumed to be N (e.g., 6) samples.

Exemplary internal processing of the similarity calculations 1104 comprises the following:

1) Lnorm(k)—normalized LeftDeltaZ(k) is calculated according to Eqn. (20):

$$Lnorm(k) = \frac{LeftDeltaZ(k) - \text{mean}[LeftDeltaZ(k)]}{\max[LeftDeltaZ(k)] - \min[LeftDeltaZ(k)]} \quad (20)$$

2) Rnorm(k)—normalized RightDeltaZ(k) is calculated according to Eqn. (21):

$$Rnorm(k) = \frac{RightDeltaZ(k) - \text{mean}[RightDeltaZ(k)]}{\max[RightDeltaZ(k)] - \min[RightDeltaZ(k)]} \quad (21)$$

3) LeftHaar(k)—scale two Haar detail coefficients of {LeftDeltaZ(k)–mean[LeftDeltaZ(k)]}, where the last 5 scale-two samples omitted from further calculations.

The approximation decomposition filter used comprises $$\left\{ \frac{\sqrt{2}}{2}, \frac{\sqrt{2}}{2} \right\};$$

the detail decomposition filter used comprises $$\left\{ -\frac{\sqrt{2}}{2}, \frac{\sqrt{2}}{2} \right\}.$$

4) RightHaar(k)—scale two Haar detail coefficients of {RightDeltaZ(k)–mean[RightDeltaZ(k)]}, with the last 5 scale-two samples omitted from further calculations.
5) Minsamples—the absolute value of the difference in samples in scale 0 (multiply by 4) between the global minimum in LeftHaar(k) and global minimum in RightHaar(k).
6) Maxsamples—the absolute value of the difference in samples in scale 0 (multiply by 4) between the global maximum in LeftHaar(k) and global maximum in RightHaar(k).
7) Sum—the sum of Minsamples and Maxsamples
8) Difference—the difference between Lnorm(k) and Rnorm(k).

Output parameters of the similarity calculation 1204 comprise:

1) MSE—the mean squared error between Lnorm(k) and Rnorm(k)
2) Mismatch—match between left and right Haar detail coefficients. If MSE $\leq$0.0185, then Mismatch=Minsamples. Otherwise, Mismatch=Sum.
3) Crossings—the number of zero crossings in Difference.
4) Maxabserr—the absolute value of the maximum difference between (Lnorm(k)–Rnorm(k))
5) Error_ratio—the ratio of Maxabserr/MSE Fuzzification—The crisp inputs are translated through membership functions into fuzzy inputs. Input parameters to the fuzzification process 1106 comprise (1) Mismatch—match between left and right Haar detail coefficients; (2) Crossings—the number of zero crossings in Difference; and (3) MSE—the mean squared error between Lnorm(k) and Rnorm(k).

Internal processing of the exemplary fuzzification process 1106 comprises: (1) M—Mismatch bounded within a predetermined range (e.g., {0,52}), with resolution of a given number (e.g. 4) of samples; and (2) C—Crossings bounded within the range e.g., {2,18}, with resolution e.g., 1.

Exemplary output parameters of the fuzzification process 1106 of FIG. 11 comprise:

1) LabelM(i)—If MSE<0.09, then one or two labels associated with M, based on Table 14 of Appendix I; otherwise, LabelM(i)={4}.
2) DegreeM(i)—If MSE<0.09, then degree associated with each M label, based on Table 15. Otherwise, DegreeM (I)={1}.
3) LabelC(i)—One or two labels associated with C, based on Table 16.
4) DegreeC(i)—Degree associated with each C label, based on Table 17.

Rule Base Inference—In the exemplary embodiment of the Delta Z similarity calculation, the fuzzy inputs from the fuzzification process 1106 of FIG. 11 are processed using the Zadeh intersection to obtain fuzzy outputs. The input parameters to this rule base inference process 1107 comprise: (1) LabelM(i)—One or two labels associated with M; (2) DegreeM(i)—Degree associated with each M label; (3) LabelC(i)—One or two labels associated with C; (4) DegreeC(i)—Degree associated with each C label; and (5) Error_ratio—the ratio of Maxabserr/MSE.

Internal processing of the inference process 1107 comprises: (1) Test1—Boolean is set to TRUE If LabelM(0)=0 AND DegreeM(0)=1; (2) Test2—Boolean is set to TRUE If LabelC(0)=1 AND DegreeC(0)=1; (3) Test3—Boolean is set to TRUE If Error_ratio >17; and (4) Testout—Boolean is calculated as (Test1 AND Test2 AND Test3).

Output parameters of the exemplary inference process comprise:

(1) LabelN(i)—One to four labels associated with Noise-Class. If Testout=FALSE, each combination of LabelM(i) and LabelC(i) is input to Table 18 (Appendix I) to determine LabelN(i). If Testout=TRUE, LabelN(0)=2.

(2) DegreeN(i)—Degree associated with each NoiseClass label. If Testout=FALSE, for each combination of LabelM(i) and LabelC(i), the minimum associated DegreeM(i) or DegreeC(i) is output as DegreeN(i). If Testout=TRUE, DegreeN(0)=1.

Defuzzification—In the exemplary embodiment of FIG. 11, the fuzzy outputs are processed to a crisp output using, e.g., the centroid method. Exemplary input parameters to the defuzzification process 1108 comprise:

1) LabelN(i)—One to four labels associated with Noise-Class.

2) DegreeN(i)—Degree associated with each NoiseClass label.

3) Minsamples—Minsamples value in current beat. This is initialized to a preselected value (e.g., +1000).

4) Minsamples(b-1)—Minsamples value from previous beat. This is initialized to a preselected value (e.g., to 0).

5) Minsamples(b-2)—Minsamples value from 2 beats past. This is initialized to a preselected value (e.g., −1000).

6) Maxabserr—the absolute value of the maximum difference between (Lnorm(k)−Rnorm(k))

7) MF(i,j)—Membership functions for NoiseClass. The row index (i) represents the label 0-4. The column index (j) represents the membership function sample. An exemplary configuration for this array is shown in Table 19 (Appendix I).

Internal processing of the exemplary defuzzification algorithm 1108 comprises determination of the following parameters:

1) F(j)—Fuzzification union. The union of the individual membership functions, with associated degrees, is taken according to Eqn. (22):

$$F(j) = \text{clip}\{DegreeN(0), MF[LabelN(0),:]\} \\ \cup \text{clip}\{DegreeN(1), MF[LabelN(1),:]\} \\ \cup \text{clip}\{DegreeN(2), MF[LabelN(2),:]\} \\ \cup \text{clip}\{DegreeN(3), MF[LabelN(3),:]\}$$ (22)

where ":" refers to using all indices j=0 to 8 and clip[x,y(j)] refers to clipping all values of the function y(j) at the maximum value of x.

2) NoiseClass1—The first temporary noise class is determined by calculating the centroid of the fuzzification union according to Eqn. (23):

$$NoiseClass1 = \frac{\sum_{j=0}^{8} F(j) \cdot (0.5j)}{\sum_{j=0}^{8} F(j)}$$ (23)

3) NoiseClass2—The second temporary noise class is determined, also with consideration of special cases such as where the natural morphology of left and right Delta Z causes high Minsample values. NoiseClass2=1 If 1) the maximum difference between all three Minsample values≦8 samples AND 2) each Minsample(i) >50 samples AND 3) MSE<0.09. Otherwise, NoiseClass2=NoiseClass1.

Output parameters of the exemplary defuzzification process 1108 comprise:

1) NoiseClassOUT—The final NoiseClass is determined, taking into account that when left and right Delta Z are associated with a small maximum absolute error, the beat is classified as quiet. NoiseClassOUT=1 If {Maxabserr<0.2 AND NoiseClass2=2}. Otherwise, NoiseClassOUT=NoiseClass2.

2) Reject Beat—Classification of beat as noisy (T=reject) or quiet (F). If NoiseClassOUT≧2, then the beat shall be considered noisy and rejected.

Figure 13A:
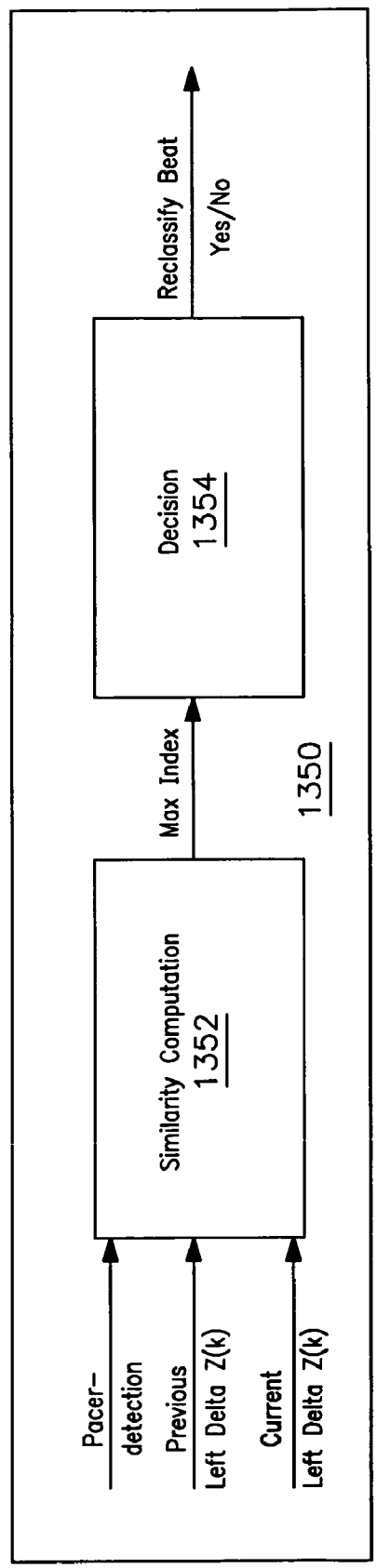
FIG. 13a is a block diagram illustrating one exemplary embodiment of the signal processing architecture used to perform the method of FIG. 13.

(iii) Referring now to FIGS. 13 and 13*a*, one exemplary embodiment of the Delta Z reproducibility algorithm 1300 is described in detail. As previously noted, the Delta Z reproducibility analysis comprises the third of three (3) Delta Z rejection criteria performed within the second level of the hierarchy of FIG. 1.

As shown in FIG. 13, the first step of the analysis comprises a comparison between the current and most recent "quiet" beats. Occasionally, when waveform artifact is present, the left and right Delta Z signals may be similar (typically, they both appear to be ramp functions), but neither resembles a typical periodic Delta Z. If the Delta Z similarity output classification is "quiet" (step 1302), then the current left Delta Z beat and most recent "quiet" left Delta Z beat are compared (step 1304) using a cross-correlation function to determine if the current beat is truly "quiet". If the degree of reproducibility is less than a first predetermined value (e.g., val1) and greater than a second value (e.g., val2) per step 1306, then the current beat is reclassified as "noisy" (step 1308). FIG. 13*a* illustrates an exemplary signal and module architecture 1350 useful for implementing this algorithm 1300 including the similarity calculation module 1352 and the decision module 1354. It will be appreciated, however, that other algorithms or architectures for analyzing beats for reproducibility may be used consistent with the invention, including using beats derived from sources other than the left side.

In the exemplary embodiment, input parameters to this Delta Z reproducibility process 1300 comprise:

1) Pacerdetection—the Boolean representing the presence of pacing spikes.

2) PreviousLeftDeltaZ(k)—samples comprising the most recent beat of Left DeltaZ(k), from the R point to most recent Q point. If this is a paced beat, the Q to R interval is assumed to be 6 samples.

3) CurrentLeftDeltaZ(k)—samples comprising the current beat of Left DeltaZ(k), from the R point to most recent Q point. If this is a paced beat, the Q to R interval is assumed to be 6 samples.

Internal processing of the exemplary reproducibility process 1300 comprises the following:

1) Start—the zeroth sample of PreviousLeftDeltaZ(k) and CurrentLeftDeltaZ(k). If Pacerdetection=FALSE, Start=(Q point+6). If Pacerdetection=TRUE, Start=(Q point+10).
2) LenPDZ—number of samples comprising PreviousLeftDeltaZ(k).
3) LenCDZ—number of samples comprising CurrentLeftDeltaZ(k).
4) PLNorm(k)—normalized PreviousLeftDeltaZ(k) is calculated as in Eqn. (24):

$$PLNorm(k) = \frac{PreviousLeftDeltaZ(k) - \text{mean}[PreviousLeftDeltaZ(k)]}{\max[PreviousLeftDeltaZ(k)] - \min[PreviousLeftDeltaZ(k)]} \quad (24)$$

5) CLNorm(k)—normalized CurrentLeftDeltaZ(k) is calculated as in Eqn. (25):

$$CLNorm(k) = \frac{CurrentLeftDeltaZ(k) - \text{mean}[CurrentLeftDeltaZ(k)]}{\max[CurrentLeftDeltaZ(k)] - \min[CurrentLeftDeltaZ(k)]} \quad (25)$$

6) Rxy(k)—cross-correlation of PLNorm(k) and CLNorm(k), which is computed as in Eqn. (26):

$$Rxy(k) = \sum_{n=0}^{N-1} PLNorm(k) \cdot CLNorm(k+n), \quad (26)$$

where $N = LenPDZ$
for $k = -(LenPDZ - 1), -(LenPDZ - 2), \ldots,$
$-2, -1, 0, 1, 2, \ldots, (LenCDZ - 1)$.

7) kmax_CC—maximum index of cross-correlation Rxy(k).

The following pseudocode illustrates one exemplary algorithmic implementation of the process of 1300 of FIGS. 13 and 13*a*.

```
// Padding the shortest Beat
//===================
padding_Length = abs(LenPDZ − LenCDZ);
if (LenPDZ < LenCDZ)
   LenDZ = LenPDZ + padding_Length;
   PLNorm(k) = [PLNorm(k) zeros(1,padding_Length)];
else
   LenDZ = LenCDZ + padding_Length;
   CLNorm(k) = [CLNorm(k) zeros(1,padding_Length)];
end
//Initialization
//=========
Begin = −LenDZ;
End = LenDZ;
x = PLNorm(k);
y = CLNorm(k);
Size = 2*LenDZ − 1;
index = 1;
```

```
//Computing the Cross_Correlation
//==========================
for k=Begin:End−2
   sum = 0;
   for i=0:LenDZ−1
      j = i + k;
      if (j<0 | j>LenDZ−1)
         continue
      else
         sum = sum + x(j)*y(i);
      end
   end
   Rxy(index) = sum;
   index = index + 1;
end
[maxi_CC,kmax_CC] = max(Rxy(k));
```

The sole output parameter of the illustrated reproducibility process 1300 comprises the MaxIndex parameter; i.e., the normalized maximum index of cross-correlation of PLNorm(k) and CLNorm(k). This parameter is computed according to Eqn. (27) below:

$$MaxIndex = \frac{kmax\_CC}{Size} \quad (27)$$

Decision—The input parameter of the exemplary decision process module 1354 of FIG. 13*a* comprises the MaxIndex parameter described immediately above. The output parameter of the decision process 1354 comprises the ReclassBeat parameter; i.e., the Boolean value representing whether the beat is quiet, or should be reclassified as noisy. The value is set to either true or false based on a predetermined range of values for MaxIndex as shown in Eqn. (28):

$$ReclassBeat = \begin{cases} \text{False} & 0.415 \leq MaxIndex \leq 0.625 \\ \text{True} & \end{cases} \quad (28)$$

Under one implementation of the present invention by the Assignee hereof, the two levels of Delta Z rejection criteria previously described herein were validated in 220 beats collected from 44 cardiac patients. These patient data were not used in algorithm training. An expert user not involved in algorithm training visually labeled each beat as rejected or non-rejected; these labels were used as reference data. During this validation, with "true positive" defined as a Delta Z beat that was correctly rejected, 90% sensitivity and 90% specificity were obtained, thereby providing experimental verification of the efficacy of this implementation of the present invention.

Parameter Median Filters

As previously discussed with respect to FIG. 1, the illustrated embodiment of the invention also utilizes a third (optional) parameter median filtering stage within the hierarchy 100. Such median filtering advantageously allows anomalous high and low values to be excluded from clinical use.

Each parameter to be filtered is input to a median filter. The length of the filter is determined by the user, e.g., selected between two values (such as 5 and 60 beats), or alternatively may be determined algorithmically (automatically) if desired. For each parameter, the filter output is also optionally displayed on the display screen of the apparatus (see the discussion of FIG. 14 presented subsequently herein) or output to another device, and stored for possible later recall.

Reasons not use such median filtering may include, e.g., to observe beat-to-beat parameter variability. This may be useful in certain circumstances such as analysis of heart rate variability. However, it is anticipated that in most applications, such filtration would be desirable.

It will be recognized that while described primarily in the context of a sequential set of processing operations (e.g., ECG rejection, then Delta Z rejection, then median filtering) as shown in the exemplary configuration of FIG. 1, the present invention may be practiced using other combinations and orders of performance. For example, in one variant, the invention allows the operator to optionally perform or not perform the median filtering operations as discussed above. In another variant, one or more portions of the ECG rejection analysis may be performed in parallel with one another. Similarly, portions of the Delta Z rejection analysis may be performed ahead of or in parallel with the ECG rejection analysis. Hence, it will be understood that the present invention is in no way limited to any specific order or sequence of steps or algorithmic operations.

Figure 10:
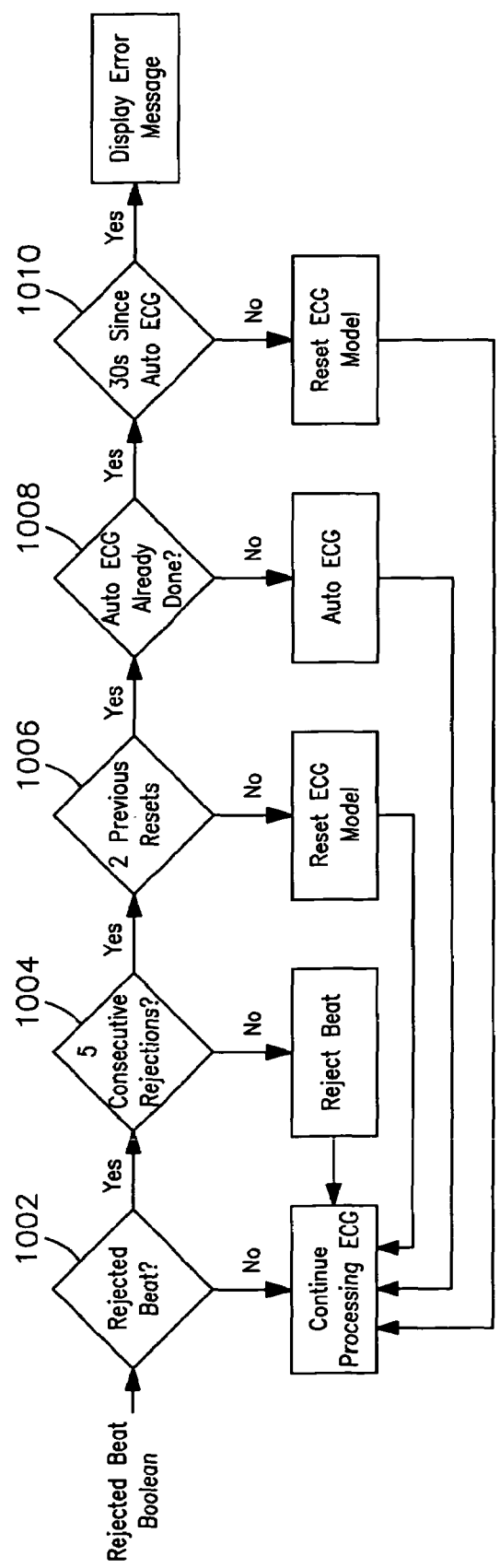
FIG. 10 is a logical flow diagram of an exemplary ECG reset module decision process.

Similarly, the logic of the exemplary embodiment of the ECG reset module described with respect to FIG. 10 may be modified in order to produced a desired functionality. For example, one of more of the conditions 1002, 1004, 1006, 1008, 1010 analyzed using this process 1000 may be removed, or others added. The order of performance may also be permuted and/or combined, such as where multiple pathways through the logic will produce an error condition. The logic may also be made contingent on other factors, such as repetition of the process 1000 (i.e., two successful cycles or iterations through the module logic generating an error condition are required before an actual error condition is invoked. Myriad other variations are possible consistent with the present invention.

Apparatus for Hemodynamic Assessment

Figure 14:
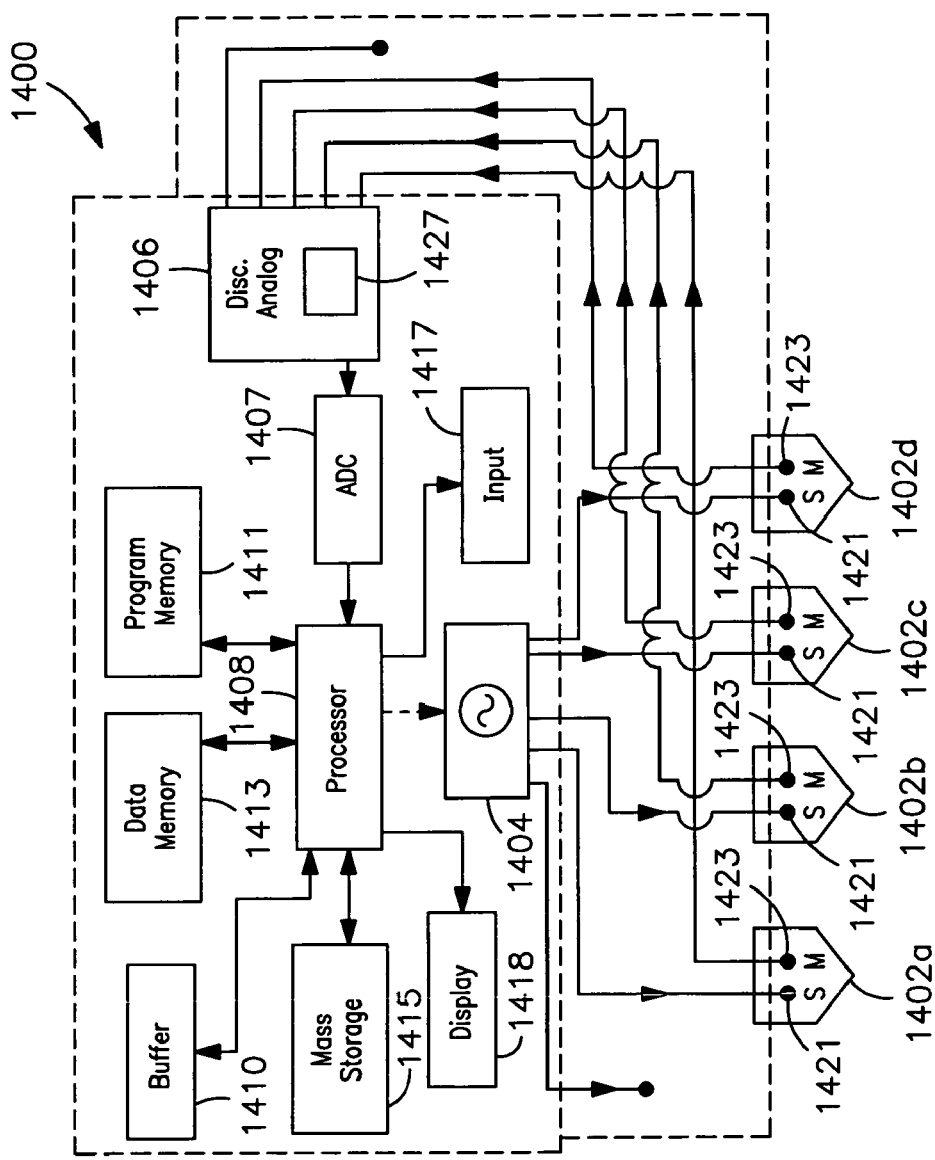
FIG. 14 is a block diagram of one exemplary embodiment of the apparatus for hemodynamic assessment according to the invention.

Referring now to FIG. 14, exemplary apparatus for measuring hemodynamic properties associated with the cardiovascular system of a living subject is described. In the illustrated embodiment, the apparatus is adapted for the measurement of the cardiac output of a human being, although it will be recognized that other parameters (hemodynamic or otherwise) and types of living organism may be evaluated in conjunction with the invention in a broader sense.

The apparatus 1400 of FIG. 14 fundamentally comprises a plurality of electrically conductive electrodes 1402 (with individual terminals 1421, 1423) for supplying a current and measuring voltage (and impedance) from the subject non-invasively; a current source 1404 coupled to at least a portion of the electrodes 1402 for providing the alternating (AC) electrical current supplied to the subject; discrete analog circuitry 1406 for preconditioning the analog impedance and ECG waveforms derived from the electrodes 1402, an analog-to-digital converter (ADC) 1407 for converting the conditioned analog signals to a binary digital format; a digital processor 1408 operatively connected to the ADC 1407 for analyzing the digital representations of the conditioned ECG and impedance waveforms; a buffer memory 1410 for storing conditioned data prior to analysis (e.g., detection of fiducial points within the waveform); program and data memories 1411, 1413, for storing program instructions and data, respectively; a mass storage device 1415, an input device 1417 for receiving operation command and data from the apparatus user, and a display device 1418 for displaying information such as data and waveforms, as well as applications program interface, to the user.

The electrodes 1402 of the embodiment of FIG. 14 comprise so-called "spot" electrodes of the type well known in the medical arts, although it will be recognized that other types of electrodes, including band electrodes may be substituted. As used herein, the term "spot" electrode includes both single- and multi-terminal electrodes adapted for use in a localized area of the subject's physiology. Exemplary configurations of the multi-terminal spot electrode especially useful with the invention herein are described in U.S. utility Pat. No. 6,636, 754 to Baura, et al. issued Oct. 21, 2003 and entitled "Apparatus and method for determining cardiac output in a living subject" as well as in U.S. design Pat. Nos. D475,138 entitled "Electrode for use on a living subject with removable protective electrode carrier", and Nos. D471,281 and D468,433 each entitled "Electrode for use on a living subject", each of the foregoing assigned to the Assignee hereof and incorporated by reference herein in its entirety.

In operation, the apparatus 1400 generates an effectively constant current (via the current source 1404) which is applied to certain ones of the terminal(s) 1421 of the electrodes 1402. The applied current derived from the current source 1404 is a 70 kHz sine wave of approximately 2.5 mA maximum RMS. The measured voltage associated with the aforementioned sine wave is on the order of 75 mV maximum RMS. These values are chosen to advantageously minimize electric shock hazard, although it will be appreciated that other frequencies, currents, or voltages may be substituted. The construction and operation of AC current sources is well known in the electronic arts, and accordingly is not described further herein.

The preprocessor 1406 and associated signal processing apparatus is in electrical communication with other electrodes 1402, from which potentials (voltages) are measured. In the selected frequency range of the AC signal (e.g., 70 kHz), the typical impedance associated with a human subject's skin is 2 to 10 times the value of the underlying thoracic impedance $Z_T(t)$. To aid in eliminating the contribution from skin and tissue impedance, the apparatus of the present invention uses at least two, and typically four electrode arrays 1402a-d for measurement, as shown in FIG. 14. In a simple application, one electrode array 1402a comprising a stimulation electrode terminal 1421 and a measurement electrode terminal 1423 is applied above the thorax of the subject, while a second electrode array 1402b (similarly having a stimulation electrode terminal and measurement electrode terminal) is applied below the thorax. The AC current from the current source is supplied to the stimulation electrode terminals 1421. Current flows from each stimulation electrode terminal 1421 through each constant skin impedance, $Z_{sk1}$ or $Z_{sk4}$, each constant body tissue impedance, $Z_{b1}$ or $Z_{b1}$, and each constant skin impedance, $Z_{sk2}$ or $Z_{sk3}$, to each measurement electrode terminal 1423. The voltages at the measurement electrode terminals 1423 are measured and input to a differential amplifier circuit 1427 within the preprocessor 1406 to obtain the differential voltage, $V_T(t)$. The desired thoracic impedance, $Z_T(t)$, is then obtained using the relationship of Eqn. (29).

$$Z_T(t) = \frac{V_T(t)}{I_T(t)} \qquad (29)$$

As shown in FIG. 14, two sets of electrode arrays 1402a-d may advantageously be used to monitor the impedance associated with the left and right portion of the thorax in the present invention. When eight electrode terminals (four arrays 1402a-d each with two terminals 1421, 1423) are used in this manner, the four measurement arrays are also used to obtain an electrocardiogram (ECG). As previously discussed, the ECG QRS interval is used to, inter alia, determine the subject's heart rate, identify the Q and R points, and perform beat rejection analysis as previously described herein.

It is noted that the apparatus 1400 described herein may be constructed in a variety of different physical configurations, using a variety of different components, and measuring a variety of different hemodynamic parameters. For example, some or even all of the foregoing components may be physically integrated (such as in an application specific integrated circuit or SoC device incorporating a DSP core, memory, "front" end analog processing, and ADC in a single piece of silicon), and/or the functionality associated with multiple components performed by a single multi-function component (e.g., a processor adapted to perform calculations associated with the event rejection methods disclosed herein, as well as host functions such as video display, bus arbitration, etc.). One exemplary configuration comprises a PC-based device of the type well known in the art, having a host microprocessor as well as the aforementioned preprocessing and signal processing functionality in the form of a separate DSP in data communication therewith. In yet another embodiment, the apparatus comprises a mobile personal computing device (such as a personal digital assistant, handheld computer or PDA), which is adapted to receive input data from the electrodes 1502 and analyze the data to produce a corrected measurement of cardiac output. It will also be recognized that other portable devices, such as laptop computers, calculators, and personal organizers, may conceivably be configured to run the computer program(s) of the present invention. Such portable devices are readily adapted to the methods of the present invention, since as a result of the invention's advantageous use of comparatively simple wavelet transforms, the processing and storage capability needed to implement the algorithm is decreased. Furthermore, a variety of different methods of transmitting the input sensor (i.e., electrode) data to these devices may be used, including networked computers, or even wireless data links.

In yet another embodiment, the apparatus 1400 comprises a "module" of the type(s) described in co-owned U.S. Pat. No. 6,602,201 to Hepp, et al. issued Aug. 5, 2003 and entitled "Apparatus and method for determining cardiac output in a living subject" incorporated herein by reference in its entirety.

Furthermore, rejected beat data, cardiac output, LVET, SV, or other measurements generated by the foregoing apparatus 1400 may also optionally be stored in the storage device 1415 for later retrieval, or output to an external device such as a printer, data storage unit, other peripheral component via a serial or parallel port if desired. Furthermore, the apparatus 1400 may be networked to another computing device or database (not shown) whereby the data generated by the apparatus may be remotely analyzed or stored. Transmission of output data to such remote devices may be accomplished using a variety of well understood methods, such as by local area network (LAN), intranet, Internet, fiber-optic systems, infrared (e.g., IrDA), or radio frequency (wireless) devices such as without limitation those complying with the IEEE-Std. 802.11, 802.15, or Bluetooth Standards.

It will be further recognized that while the apparatus 1400 of the invention is described herein as a substantially discrete or "stand-alone" system, the invention may be adapted to act as a plug in card, module, or other complementary device (including any supporting software) for an existing ECG or patient monitoring system that utilizes electrodes. Hence, the invention can advantageously be retrofitted to such prior art systems, thereby extending the utility of the pre-existing system, and potentially obviating the purchase of entirely new equipment.

Furthermore, the apparatus 1400 may comprise part of a computer network, such as LAN, WLAN, piconet, scatternet, internet, etc., where data connectivity between the various entities on the network is provided. For example, in one embodiment, the apparatus 1400 comprises an ECG or ICG module within a parent monitoring system of the type previously referenced. The module (and/or parent system) may be in wireless data communication with a local WLAN node (e.g., an 802.11 AP or Bluetooth Master) servicing a plurality of homogeneous or heterogeneous devices. The WLAN node is in communication over, e.g., an IEEE-Std. 802.3 Ethernet network of the like, with one or more other local or remote nodes. In this fashion, a large care facility can remain in data communication with the individual apparatus 1400 via one (or more) centralized monitoring or provisioning stations.

A client/server architecture may also be used, wherein each of the ECG/ICG modules acts as a client device (including optionally running a distributed application on the module and an associated server). Myriad other network configurations will be appreciated by those of ordinary skill in the networking arts provided the present disclosure.

Similarly, the apparatus 1400 may comprise an ECG or ICG module having a portable client device associated therewith for control of one or more module functions. The client device may comprise, e.g., a handheld PDA or the like having a wireless interface to the module.

Computer Program

A computer program for implementing the aforementioned methods event analysis and rejection is now described. In one exemplary embodiment, the computer program comprises an object ("machine") code representation of an assembly source code listing implementing the analytical methodologies previously described herein (including, e.g., the hierarchical analysis framework of FIG. 1), either individually or in combination thereof. While assembly language is used for the present embodiment, it will be appreciated that other programming languages may be used, including for example VisualBasic™, Fortran, C, and C++. The object code representation of the source code listing is compiled and disposed on a media storage device of the type well known in the computer arts. Such media storage devices can include, without limitation, optical discs, CD ROMs, magnetic floppy disks or "hard" drives, volatile or non-volatile memory ICs, tape drives, flash memory, USB keys, or even magnetic bubble memory. The computer program further comprises a user interface (e.g., GUI) of the type well known in the programming arts, which is operatively coupled to the display and input device of the host computer or apparatus 1400 on which the program is run.

In terms of general structure, the program is in one embodiment comprised of a series of subroutines or algorithms for implementing the methodologies described herein based on measured physiologic data (e.g., the "inputs" previously defined) which are provided to the host computer. In a second embodiment, the computer program comprises an assembly language/micro-coded instruction set or firmware disposed within the embedded storage device, i.e. program memory, of a digital signal processor (DSP) or microprocessor associated with the foregoing hemodynamic measurement apparatus of FIG. 14.

The various functions of the present embodiment may also run and/or be controlled at other layers of the device protocol stack; e.g., substantially as part of any O/S or "middleware" of the parent platform if desired, thereby making the operation of the program transparent to the user.

Method of Providing Treatment

Figure 15:
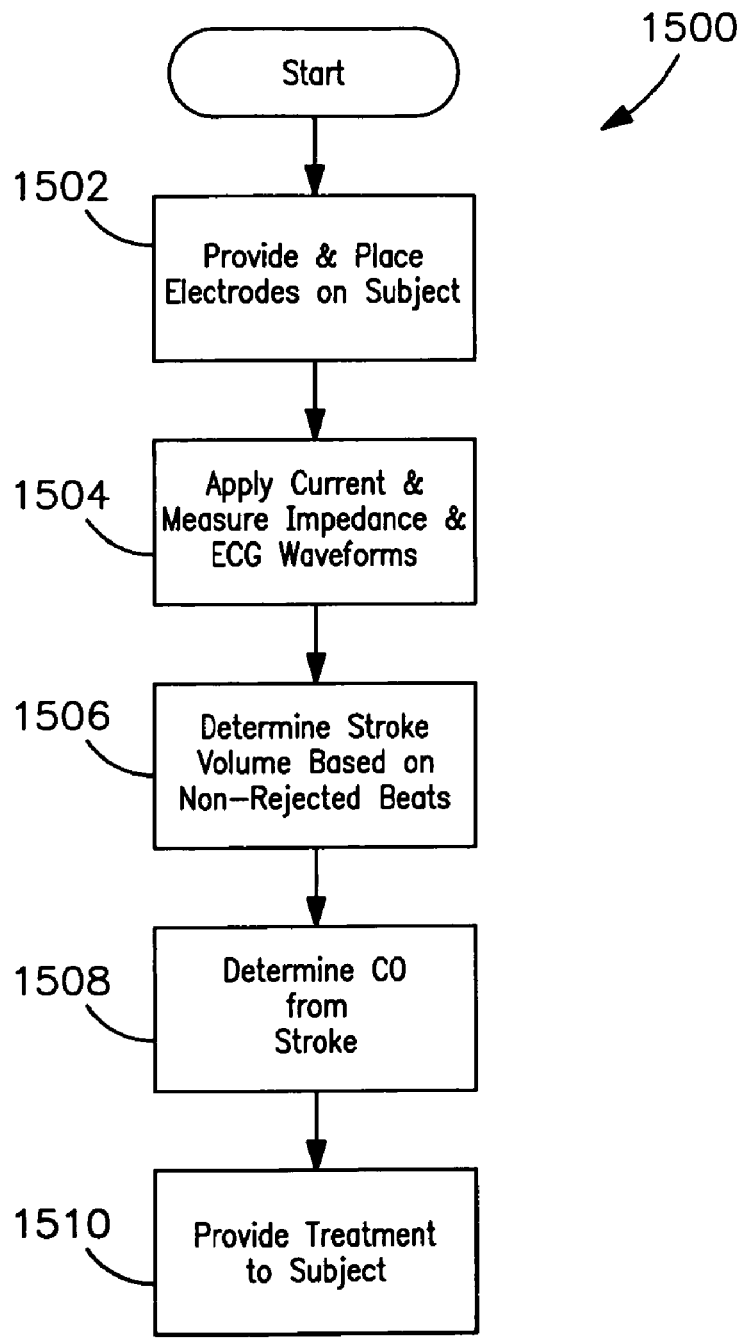
FIG. 15 is a logical flow diagram illustrating one exemplary embodiment of the method of providing treatment to a subject using the aforementioned methods.

Referring now to FIG. 15, a method of providing treatment to a subject using the aforementioned methods of waveform analysis and event rejection is described. While the following discussion is cast in terms of the aforementioned methods and algorithms adapted for determining cardiac output, it will be recognized that the method or providing treatment described herein is more broadly applicable to treatment based on the assessment of any physiologic property or parameter utilizing event rejection.

As shown in FIG. 15, the method of providing treatment 1500 generally comprises first disposing a plurality of impedance cardiography electrodes with respect to the thoracic cavity of the subject per step 1502. As previously discussed, the electrodes 1402 may comprise the multi-terminal type described above with respect to FIG. 15 (or other suitable configuration), and are disposed above and below the thorax of the subject such that at least one stimulation terminal and one excitation terminal are above and below the thorax. Next, the impedance waveform (and ECG) data of the subject are obtained non-invasively via the electrodes 1402 per step 1504; specifically by applying a constant AC waveform to the stimulation terminal(s), and measuring the resultant voltage at the measurement terminal(s). In step 1506, the stroke volume of the subject's cardiac muscle during at least one cardiac cycle is determined using beats that have been analyzed using the analytical techniques previously discussed herein. Specifically, the source ECG waveform is analyzed and beats rejected, and the remaining beats are used as the basis of subsequent LVET and $dZ/dt_{max}$ calculations. The stroke volume is then determined from the derived values of LVET and $dZ/dt_{max}$. The cardiac output (CO) of the subject is next determined in step 1508 based on the stroke volume determined in step 1506, and the heart rate (HR) derived from the subject from the ECG waveform.

Lastly, a course of treatment is determined and provided to the subject based on the cardiac output (CO) of step 1508. Such course of treatment may include, for example, the intravenous injection of pharmacological agents, pacemaker implantation, or other such measures aimed at increasing cardiac output or otherwise stemming further degradation of the subject's cardiac function.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

Appendix I—Tables

TABLE 1

LabelRR(i) Table

| M_rr | LabelRR(0) | LabelRR(1) |
|---|---|---|
| 0 | 0 | |
| 1 | 0 | |
| 2 | 0 | 1 |
| 3 | 1 | |
| 4 | 1 | 2 |
| 5 | 2 | |
| 6 | 2 | |
| 7 | 2 | 3 |
| 8 | 3 | |
| 9 | 4 | |

TABLE 2

DegreeRR(i) Table

| M_rr | DegreeRR(0) | DegreeRR(1) |
|---|---|---|
| 0 | 1 | |
| 1 | 1 | |
| 2 | 0.5 | 0.5 |
| 3 | 1 | |
| 4 | 0.5 | 0.5 |
| 5 | 1 | |
| 6 | 1 | |
| 7 | 0.5 | 0.5 |
| 8 | 1 | |
| 9 | 1 | |

TABLE 3

LabelMSE(i) Table

| M_mse | LabelMSE(0) | LabelMSE(1) |
|---|---|---|
| 0 | 0 | |
| 1 | 0 | 1 |
| 2 | 1 | |
| 3 | 2 | |
| 4 | 2 | 3 |
| 5 | 2 | 3 |
| 6 | 3 | |
| 7 | 3 | |
| 8 | 3 | |
| 9 | 3 | 4 |
| 10 | 4 | |

TABLE 4

DegreeMSE(i) Table

| Msymfact | DegreeSf(0) | DegreeSf(1) |
|---|---|---|
| 0 | 1 | |
| 1 | 0.5 | 0.5 |
| 2 | 1 | |
| 3 | 1 | |
| 4 | 0.67 | 0.33 |
| 5 | 0.33 | 0.67 |
| 6 | 1 | |

TABLE 4-continued

DegreeMSE(i) Table

| Msymfact | DegreeSf(0) | DegreeSf(1) |
|---|---|---|
| 7 | 1 | |
| 8 | 1 | |
| 9 | 0.5 | 0.5 |
| 10 | 1 | |

TABLE 5

Rule Base Inference for LabelNR

| | LabelRR(i) | | | | |
|---|---|---|---|---|---|
| LabelMSE(i) | 0 | 1 | 2 | 3 | 4 |
| 0 | 0 | 0 | 0 | 0 | 1 |
| 1 | 0 | 0 | 1 | 1 | 2 |
| 2 | 0 | 0 | 1 | 3 | 4 |
| 3 | 1 | 1 | 3 | 4 | 4 |
| 4 | 3 | 4 | 4 | 4 | 4 |

TABLE 6

NoiseClass membership functions.

| Mem Func | Sample | | | | |
|---|---|---|---|---|---|
| | 0 | 1 | 2 | 3 | 4 |
| 0 | 1 | 0 | 0 | 0 | 0 |
| 1 | 0 | 1 | 0 | 0 | 0 |
| 2 | 0 | 0 | 1 | 0 | 0 |
| 3 | 0 | 0 | 0 | 1 | 0 |
| 4 | 0 | 0 | 0 | 0 | 1 |

TABLE 7

Reverse Biorthogonal 2.2 lowpass filter coefficients

| $b_{H0}$ to $b_{H10}$ | $b_{H11}$ to $b_{H22}$ | $b_{H23}$ to $b_{H32}$ |
|---|---|---|
| 0 | 0.375 | 0.250 |
| 0 | 0.500 | 0.125 |
| 0 | 0.625 | 0 |
| 0 | 0.750 | 0 |
| 0 | 0.875 | 0 |
| 0 | 1.000 | 0 |
| 0 | 0.875 | 0 |
| 0 | 0.750 | 0 |
| 0 | 0.625 | 0 |
| 0.125 | 0.500 | 0 |
| 0.250 | 0.375 | 0 |

TABLE 8

LabelCp(i) Table

| Mcenterpt | LabelCp(0) | LabelCp(1) |
|---|---|---|
| 0 | 0 | |
| 1 | 0 | |
| 2 | 0 | |
| 3 | 0 | |
| 4 | 0 | |
| 5 | 0 | 1 |
| 6 | 1 | |
| 7 | 1 | |
| 8 | 1 | |

TABLE 8-continued

LabelCp(i) Table

| Mcenterpt | LabelCp(0) | LabelCp(1) |
|---|---|---|
| 9 | 1 | 2 |
| 10 | 2 | |
| 11 | 2 | 3 |
| 12 | 3 | |
| 13 | 3 | |
| 14 | 3 | |
| 15 | 3 | 4 |
| 16 | 4 | |

TABLE 9

DegreeCp(i) Table

| Mcenterpt | DegreeM(0) | DegreeM(1) |
|---|---|---|
| 0 | 1 | |
| 1 | 1 | |
| 2 | 1 | |
| 3 | 1 | |
| 4 | 1 | |
| 5 | 0.5 | 0.5 |
| 6 | 1 | |
| 7 | 1 | |
| 8 | 1 | |
| 9 | 0.5 | 0.5 |
| 10 | 1 | |
| 11 | 0.5 | 0.5 |
| 12 | 1 | |
| 13 | 1 | |
| 14 | 1 | |
| 15 | 0.5 | 0.5 |
| 16 | 1 | |

TABLE 10

LabelSf(i) Table

| Msymfact | LabelSf(0) | LabelSf(1) |
|---|---|---|
| 0 | 0 | |
| 1 | 0 | |
| 2 | 0 | 1 |
| 3 | 1 | |
| 4 | 1 | 2 |
| 5 | 2 | |
| 6 | 2 | 3 |
| 7 | 3 | |
| 8 | 3 | |
| 9 | 3 | 4 |
| 10 | 4 | |

TABLE 11

DegreeSf(i) Table

| Msymfact | DegreeSf(0) | DegreeSf(1) |
|---|---|---|
| 0 | 1 | |
| 1 | 1 | |
| 2 | 0.5 | 0.5 |
| 3 | 1 | |
| 4 | 0.5 | 0.5 |
| 5 | 1 | |
| 6 | 0.5 | 0.5 |
| 7 | 1 | |
| 8 | 1 | |
| 9 | 0.5 | 0.5 |
| 10 | 1 | |

TABLE 12

Rule Base Inference for LabelR

| LabelSf(i) | LabelCp(i) | | | | |
|---|---|---|---|---|---|
| | 0 | 1 | 2 | 3 | 4 |
| 0 | 4 | 0 | 0 | 0 | 4 |
| 1 | 4 | 1 | 0 | 1 | 4 |
| 2 | 4 | 3 | 1 | 3 | 4 |
| 3 | 4 | 4 | 2 | 4 | 4 |
| 4 | 4 | 4 | 4 | 4 | 4 |

TABLE 13

NoiseClass membership functions

| Mem Func | Sample | | | | |
|---|---|---|---|---|---|
| | 0 | 1 | 2 | 3 | 4 |
| 0 | 1 | 0 | 0 | 0 | 0 |
| 1 | 0 | 1 | 0 | 0 | 0 |
| 2 | 0 | 0 | 1 | 0 | 0 |
| 3 | 0 | 0 | 0 | 1 | 0 |
| 4 | 0 | 0 | 0 | 0 | 1 |

TABLE 14

LabelM(i) Table

| M | LabelM(0) | LabelM(1) |
|---|---|---|
| 0 | 0 | |
| 1 | 0 | |
| 2 | 0 | 1 |
| 3 | 1 | |
| 4 | 1 | 2 |
| 5 | 2 | |
| 6 | 2 | 3 |
| 7 | 3 | |
| 8 | 3 | |
| 9 | 3 | |
| 10 | 3 | |
| 11 | 3 | 4 |
| 12 | 4 | |
| 13 | 4 | |

TABLE 15

DegreeM(i) Table

| M | DegreeM(0) | DegreeM(1) |
|---|---|---|
| 0 | 1 | |
| 1 | 1 | |
| 2 | 0.5 | 0.5 |
| 3 | 1 | |
| 4 | 0.5 | 0.5 |
| 5 | 1 | |
| 6 | 0.5 | 0.5 |
| 7 | 1 | |
| 8 | 1 | |
| 9 | 1 | |
| 10 | 1 | |
| 11 | 0.5 | 0.5 |
| 12 | 1 | |
| 13 | 1 | |

TABLE 16

LabelC(i) Table

| C | LabelC(0) | LabelC(1) |
|---|---|---|
| 0 | 0 | |
| 1 | 1 | |
| 2 | 1 | |
| 3 | 1 | 2 |
| 4 | 1 | 2 |
| 5 | 1 | 2 |
| 6 | 2 | |
| 7 | 2 | 3 |
| 8 | 3 | |
| 9 | 3 | |
| 10 | 3 | |
| 11 | 3 | |
| 12 | 3 | |
| 13 | 3 | 4 |
| 14 | 3 | 4 |
| 15 | 3 | 4 |
| 16 | 4 | |

TABLE 17

DegreeC(i) Table

| C | DegreeC(0) | DegreeC(1) |
|---|---|---|
| 0 | 1 | |
| 1 | 1 | |
| 2 | 1 | |
| 3 | 0.75 | 0.25 |
| 4 | 0.5 | 0.5 |
| 5 | 0.25 | 0.75 |
| 6 | 1 | |
| 7 | 0.5 | 0.5 |
| 8 | 1 | |
| 9 | 1 | |
| 10 | 1 | |
| 11 | 1 | |
| 12 | 1 | |
| 13 | 0.75 | 0.25 |
| 14 | 0.5 | 0.5 |
| 15 | 0.25 | 0.75 |
| 16 | 1 | |

TABLE 18

Rule Base Inference for LabelN

| LabelM(i) | LabelC(i) | | | | |
|---|---|---|---|---|---|
| | 0 | 1 | 2 | 3 | 4 |
| 0 | 2 | 1 | 0 | 0 | 0 |
| 1 | 2 | 1 | 1 | 1 | 1 |
| 2 | 2 | 2 | 1 | 1 | 2 |
| 3 | 3 | 2 | 2 | 2 | 3 |
| 4 | 4 | 4 | 3 | 3 | 4 |

TABLE 19

NoiseClass membership functions

| Mem Func | Sample | | | | | | | | |
|---|---|---|---|---|---|---|---|---|---|
| | 0 | 1 | 2 | 3 | 4 | 5 | 6 | 7 | 8 |
| 0 | 1 | 0.5 | 0 | 0 | 0 | 0 | 0 | 0 | 0 |
| 1 | 0 | 0.5 | 1 | 0.5 | 0 | 0 | 0 | 0 | 0 |
| 2 | 0 | 0 | 0 | 0.5 | 1 | 0.5 | 0 | 0 | 0 |

TABLE 19-continued

| | NoiseClass membership functions | | | | | | | | |
|---|---|---|---|---|---|---|---|---|---|
| Mem | Sample | | | | | | | | |
| Func | 0 | 1 | 2 | 3 | 4 | 5 | 6 | 7 | 8 |
| 3 | 0 | 0 | 0 | 0 | 0 | 0.5 | 1 | 0.5 | 0 |
| 4 | 0 | 0 | 0 | 0 | 0 | 0 | 0 | 0.5 | 1 |

What is claimed is:

1. Apparatus adapted to evaluate the cardiac beats of a living subject, said apparatus comprising programmable medium having at least one fuzzy-based noise algorithm and at least one fuzzy-based morphology algorithm.

2. The apparatus of claim 1, wherein said at least one morphology algorithm comprises generation of a Scale 1 wavelet filter.

3. The apparatus of claim 2, wherein said Scale 1 filter is calculated based on a reverse biorthogonal 2.2 wavelet.

4. Impedance cardiographic apparatus adapted to evaluate physiologic waveforms obtained from a living subject using programmable media adapted to contain a computer program thereon, said computer program adapted to store and evaluate criteria comprising (i) at least one ECG rejection criterion and (ii) at least one Delta Z rejection criterion.

5. The apparatus of claim 4, wherein said computer program comprises a fuzzy logic model adapted to perform said evaluation of said ECG rejection criterion.

6. The apparatus of claim 5, wherein said computer program comprises a fuzzy logic model adapted to perform said evaluation of said Delta Z rejection criterion.

7. The apparatus of claim 6, wherein said computer program is further adapted to apply median filtering to at least one parameter associated with said waveforms.

8. The apparatus of claim 4, wherein said apparatus is further adapted to receive at least one impedance waveform, and generate estimates of cardiac output (CO) based at least in part on said physiologic waveforms and said at least one impedance waveform.

9. The apparatus of claim 8, wherein said generation of estimates of CO is performed at least in part using wavelet transforms.

10. The apparatus of claim 9, wherein said wavelet transforms are used in detecting a plurality of fiducial points associated with at least one of said physiologic waveforms and said at least one impedance waveform.

11. The apparatus of claim 4, wherein said physiologic waveforms comprise ECG and impedance waveforms.

12. The apparatus of claim 11, wherein wavelet transforms are used to detecting a plurality of fiducial points associated with at least one of said physiologic waveforms.

13. Cardiographic apparatus adapted to comprise media adapted to contain a computer program configured to store one or more criteria and evaluate the cardiac beats of a living subject using:
    an ECG rejection analysis;
    a Delta Z rejection analysis; and
    a median filtering analysis.

14. The apparatus of claim 13, wherein said ECG rejection analysis comprises an ECG noise analysis and an ECG morphology analysis.

15. The apparatus of claim 13, wherein said Delta Z rejection analysis comprises an analysis selected from the group consisting of: (i) a Delta Z similarity analysis and (ii) a Delta Z reproducibility analysis.

16. The apparatus of claim 14, wherein said Delta Z rejection analysis comprises an analysis selected from the group consisting of: (i) a Delta Z similarity analysis and (ii) a Delta Z reproducibility analysis.

17. The apparatus of claim 13, wherein said ECG rejection, said Delta Z rejection, and said median filter analyses are performed in sequential order.

18. A method of evaluating the cardiac beats of a living subject, comprising:
    performing an ECG rejection analysis;
    performing a Delta Z rejection analysis; and
    performing a median filtering analysis.

19. The method of claim 18, wherein said act of performing an ECG rejection analysis comprises performing an ECG noise analysis and an ECG morphology analysis.

20. The method of claim 18, wherein said act of performing a Delta Z rejection analysis comprises performing an analysis selected from the group consisting of: (i) a Delta Z similarity analysis and (ii) a Delta Z reproducibility analysis.

21. The method of claim 19, wherein said act of performing a Delta Z rejection analysis comprises performing an analysis selected from the group consisting of: (i) a Delta Z similarity analysis and (ii) a Delta Z reproducibility analysis.

22. A method of assessing cardiac output within a living subject, comprising:
    disposing a plurality of electrodes relative to the thoracic cavity of said subject;
    passing an electrical current through at least a portion of said thoracic cavity;
    measuring at least one impedance waveform associated with said thoracic cavity using said current and at least one of said plurality of electrodes;
    measuring at least electrocardiographic waveform having a plurality of cardiac beats associated therewith;
    selectively rejecting at least one of said cardiac beats, said rejecting comprising evaluating a plurality of said beats using a multi-level hierarchical analysis algorithm; and
    determining cardiac output based at least in part on said impedance waveform and at least a portion of the non-rejected ones of said cardiac beats.

23. The method of claim 22, further comprising processing said at least one impedance waveform to identify a plurality of B,C,X, and O points of $\Delta Z$ and $dZ/dt$ waveforms.

24. The method of claim 23, wherein the act of determining cardiac output comprises determining left ventricular ejection time (LVET).

25. The method of claim 24, wherein the act of determining LVET comprises determining the difference between respective ones of said plurality of X and B points.

26. A method of assessing cardiac output within a living subject, comprising:
    disposing a plurality of electrodes relative to the thoracic cavity of said subject;
    passing an electrical current through at least a portion of said thoracic cavity;
    measuring at least one impedance waveform associated with said thoracic cavity using said current and at least one of said plurality of electrodes;
    measuring at least electrocardiographic waveform having a plurality of events associated therewith;
    selectively rejecting at least one of said events, said rejecting comprising evaluating a plurality of cardiac beats based on (i) one or more ECG rejection criteria; and (ii) one or more Delta Z rejection criteria; and
    determining cardiac output based at least in part on said impedance waveform and at least a portion of the non-rejected ones of said events.

27. The method of claim 26, further comprising evaluating said plurality of beats using at least one parameter median filter.

28. The method of claim 26, further comprising processing said at least one impedance waveform to identify a plurality of B,C,X, and O points of ΔZ and dZ/dt waveforms.

29. The method of claim 26, wherein the act of determining cardiac output comprises determining left ventricular ejection time (LVET).

30. The method of claim 26, wherein the act of determining LVET comprises determining the difference between respective ones of said plurality of X and B points.

31. A method of assessing a hemodynamic parameter within a living subject, comprising:
    disposing at least one electrode relative to said subject;
    measuring at least one cardiographic waveform from said subject using said at least one electrode, said waveform having a plurality of beats;
    processing said plurality of beats to identify first beats that should be rejected, and second beats that should not be rejected, said processing comprising evaluating plurality of beats with respect to at least one noise criterion and at least one morphology criterion; and
    assessing said hemodynamic parameter based at least in part on said second beats.

32. The method of claim 31, wherein said at least one noise criterion comprises a fuzzy logic analysis.

33. The method of claim 31, wherein said at least one noise and morphology criteria are conducted sequentially.

34. A method of assessing a hemodynamic parameter within a living subject, comprising:
    disposing at least one electrode relative to said subject;
    measuring at least one cardiographic waveform from said subject using said at least one electrode, said waveform having a plurality of beats;
    processing said plurality of beats to identify first beats that should be rejected, and second beats that should not be rejected, said processing comprising generating a Scale 1 wavelet filter; and
    assessing said hemodynamic parameter based at least in part on said second beats.

35. The method of claim 34, wherein said Scale 1 filter is calculated based on a reverse biorthogonal 2.2 wavelet.

36. A method of evaluating the cardiac beats of a living subject, comprising:
    performing a beat rejection analysis on a plurality of said cardiac beats, said beat rejection analysis comprising at least performing a morphology analysis;
    rejecting at least one of said beats as part of said rejection analysis;
    determining, based at least in part on said at least one rejected beat, a status of said rejection analysis, said act of determining a status comprising at least determining whether inputs to said morphology process are proper by at least evaluating the number of consecutive beat rejections including said at least one rejected beat; and
    when said determination indicates that more than a predetermined number of consecutive beats has occurred, utilizing an automatic ECG vector process to identify at least one proper input.

37. A method of evaluating the cardiac beats of a living subject, comprising:
    providing a plurality of sources of said cardiac beats;
    performing a beat rejection analysis on a plurality of said cardiac beats derived from a first of said plurality of sources;
    rejecting at least one of said beats as part of said analysis;
    determining, based at least in part on said at least one rejected beat, the suitability of said first source for providing said cardiac beats; and
    selecting a second of said sources as an input to said beat rejection analysis when said act of determining indicates that said first source is not suitable;
    wherein said act of selecting comprises performing an auto-ECG vector analysis.

38. The method of claim 37, wherein said act of determining comprises evaluating at least one of (i) the number of consecutive beats rejected, and/or (ii) the number of resets of said beat rejection analysis previously performed.

39. A method of evaluating substantially periodic events within a time-variant waveform, comprising:
    providing a plurality of sources of said events;
    performing an event rejection analysis on a plurality of said events derived from a first of said plurality of sources;
    rejecting at least one of said events as part of said analysis; and
    determining, based at least in part on said at least one rejected event, the suitability of said first source for providing said events;
    wherein said events comprise Gaussian monopulses within a time-modulated ultrawideband communication system.

40. The method of claim 39, wherein said events comprise active acoustic pulses within a sonar or underwater acoustic profiling system.

41. The method of claim 39, wherein said events comprise pulses within a pulsed radio frequency (RF) system.

42. Apparatus adapted to evaluate the cardiac beats of a living subject, said apparatus comprising:
    a processor;
    a storage device in data communication with said processor; and
    at least one computer program resident in said storage device and adapted to run on said processor, said at least one program comprising:
        at least one fuzzy-based noise algorithm; and
        at least one fuzzy-based morphology algorithm.

43. The apparatus of claim 42, wherein said at least one morphology algorithm comprises generation of a wavelet filter.

44. The apparatus of claim 43, wherein said filter is calculated based on a reverse biorthogonal wavelet.

45. The apparatus of claim 42, wherein said apparatus comprises an impedance cardiographic (ICG) device.

* * * * *